US008703099B2

(12) United States Patent
Reis et al.

(10) Patent No.: US 8,703,099 B2
(45) Date of Patent: Apr. 22, 2014

(54) REGISTRY METHOD AND CONTROL SYSTEM FOR DEA SCHEDULE II-V MEDICINES

(75) Inventors: Alan J. Reis, Pittsburgh, PA (US); Christian Schafmeister, Pittsburgh, PA (US)

(73) Assignee: DR Pharma Nova, LLC, Greenburg, PA (US)

( * ) Notice: Subject to any disclaimer, the term of this patent is extended or adjusted under 35 U.S.C. 154(b) by 893 days.

(21) Appl. No.: 11/922,794

(22) PCT Filed: Feb. 23, 2006

(86) PCT No.: PCT/US2006/006730
§ 371 (c)(1),
(2), (4) Date: Sep. 5, 2008

(87) PCT Pub. No.: WO2006/091885
PCT Pub. Date: Aug. 31, 2006

(65) Prior Publication Data
US 2009/0208413 A1 Aug. 20, 2009

Related U.S. Application Data

(60) Provisional application No. 60/656,232, filed on Feb. 24, 2005.

(51) Int. Cl.
*A61K 49/00* (2006.01)

(52) U.S. Cl.
USPC ............. 424/9; 548/302.7; 549/200; 585/407

(58) Field of Classification Search
USPC ............. 424/9; 549/200; 548/302.7; 585/407
See application file for complete search history.

(56) References Cited

U.S. PATENT DOCUMENTS

| 3,433,791 A | 3/1969 | Bentley |
| 6,399,609 B1 | 6/2002 | Wilde |
| 6,687,676 B1 | 2/2004 | Denny |

FOREIGN PATENT DOCUMENTS

| GB | 1136214 | 12/1968 |
| WO | WO9111172 | 8/1991 |
| WO | WO9402518 | 2/1994 |
| WO | WO9855148 | 12/1998 |
| WO | WO0200196 | 1/2002 |

OTHER PUBLICATIONS

Sternbach, L.H., et al, "Quinazolines and I, 4-Benzodiazepines. X1 Nitro-Substituted 5-Phenyl-1, 4-benzodiazepine Derivatives," *Journal of Medicinal Chemistry*, (Sep. 5, 1962) vol. 6, pp. 261-265.
Walser, A., et al, "Triazolobenzo- and Triazolothienodiazepines as Potent Antagonists of Platelet Activating Factor," *Journal of Medicinal Chemistry*, (Jul. 25, 1990) vol. 34, pp. 1209-1221.
Thai, D.L., et al, "Asymmetric Synthesis and Pharmacology of Methylphenidate and Its Para-Substituted Derivatives," *Journal of Medicinal Chemistry*, (Sep. 12, 1997) vol. 41, pp. 591-601.
Kenner, C. R., "A Rapid, High-Yield Conversion of Codeine to Morphine," *Journal of Medicinal Chemistry*, (May 3, 1976) vol. 20, pp. 164-165.
Novakov, C.P., et al, "An ESR and HPLC-EC Assay for the Detection of Alkyl Radicals," *Chemical Residual Toxicology* (Apr. 3, 2001) vol. 14, pp. 1239-1246.
Mukade, T., et al, "Parallel Solution-Phase Asymmetric Synthesis of α-Branched Amines" *Journal of Combinatorial Chemistry*, (Feb. 12, 2003) vol. 5, pp. 590-596.
Lopez, D., et al, "The [4+2] Additional of Singlet Oxygen to Thebaine: New Access to Highly Functionalized Morphine Derivatives via Opioid Endoperoxides" *Journal of Organic Chemistry*, (Mar. 2, 2000) vol. 65, pp. 4671-4678.
Liu, G., et al, "Catalytic Asymmetric Synthesis of tert-Butanesulfinamide. Application to the Asymmetric Synthesis of Amines," *Journal of American Chemical Society*, (Jun. 18, 1997) vol. 119, pp. 9913-9914.
Kotick, M.P., et al, "Analgesic Narcotic Antagonists. 1. 8β-Alkyl-, 8β-Acyl, and 8β- (Tertiary Alcohol) Dihydrocodeinones and—Dihydromorphinones," *Journal of Medicinal Chemistry*, (Jun. 15, 1979) vol. 23, pp. 166-174.
Konosu, T., et al, "Triazole Antifungals. IV. Synthesis and Antifungal Activies of 3-Acylamino-2aryl-2-butanol Derivatives," *Chemical and Pharmaceutical Bulletin*, (Mar. 25, 1991) vol. 39, Issue 10, pp. 2581-2589.
Iijima, I., et al, "Synthesis and Antinocieceptive Activity of 7-Methoxycodeine" *Journal of Medicinal Chemistry*, (May 18, 1978) vol. 21, No. 12, pp. 1320-1322.
Blaney, P., et al, "Solid-Phase Synthesis of Tertiary Methylamines Via Reductive Alkylation-Fragmentation Using a Hydroxylamine Linker," *Tetrahedron Letters*, (Jun. 5, 2000) vol. 41, pp. 6635-6638.
Bartroli, J., et al, "New Azole Antifungals. 2. Synthesis and Antifungal Activity of Heterocyclecarboxamide Derivatives of 3-Amino-3-aryl-1-azoly1-2-butanol," *Journal of Medicinal Chemistry*, (Oct. 24, 1997) vol. 41, pp. 1855-1868.
Ashton, H., "The Treatment of Benzodiazepine Dependence," *Addiction* (1994) vol. 89, pp. 1535-1541.

(Continued)

*Primary Examiner* — Paul V. Ward
(74) *Attorney, Agent, or Firm* — Workman Nydegger

(57) ABSTRACT

The present invention provides compositions and methods for synthesizing labeled drugs. The present invention further provides methods for preventing or stopping prescription drug abuse for all agents registered as a Drug Enforcement Agency (DEA) schedule II through schedule V medications. According to the present invention, methods are provided for monitoring patient compliance with prescribed drug treatment. The present invention also provides methods for facilitating a replacement prescription when a patient is left without access to their prescribed drug. Furthermore, the present invention provides a method to improve employee compliance with an employer's drug policies via either a voluntary or compulsory system for enhanced drug testing.

13 Claims, 17 Drawing Sheets

(56) References Cited

OTHER PUBLICATIONS

Seivewright, N., "Benzodiazepines in the Illicit Drug Scene," Presented at the Second International Conference on the Reductions of Drug-Related Harm, Barcelona, Spain (Apr. 1991).

Voges, R., et al, "Synthesis and Applications of Isotopically Labelled Compounds," *International Symposium on the Synthesis and Applicatons of Isotopes and Isotopically Labelled Compounds,* (Jun. 5, 1994: Strasboug, France) pp. 1-26.

Beard, C.D., et al, "Reactions of Silver Perchlorate and of Silver Triflate with Alkyl Iodides, Solvent Inhibition of Isomerization," *Journal of Organic Chemistry,* (Aug. 1, 1974) vol. 39, No. 26, pp. 3875-3877.

Fujii, I., et al, "An Expedient and Selective Route to Crowned Morphine and Isomorphine Congeners. A Prob for Ionophore and Molecular Recognition of Opiate Receptor," *Tetrahedron Letters* (1984) vol. 25, Issue 31, pp. 3335-3338.

Bullock, R.M., et al, "Intramolecular Hydrogen Exchange Among the Coordinated Methane Fragments of Cp2W(H)CH3. Evidence for the Formation of a .sigma. Complex of Methane Prior to Elimination," *Journal of the American Chemical Society,* (May 1989) vol. 111, No. 11, pp. 3897-3908.

Gates, M., "The Conversion of Codeinone to Codeine" *Journal of the American Chemical Society,* (Sep. 1953) vol. 75, No. 17, pp. 4340-4341.

Koves, G.J., "Synthesis of Deuterium Labelled Lorazepam," *Journal of Labelled Compounds and Radiopharmaceuticals,* (1991), vol. 29, pp. 15-22.

Brine, G.A., et al, "Carbon-13 Nuclear Magnetic Resonance Spectra of Fentanyl Analogs," *Journal of Heterocyclic Chemistry,* (May/Jun. 1989) vol. 26, Issue 3, pp. 677-686.

Fryer, R.I., et al, "Quinazolines and 1,4-benzodiazepines. XLIV. Formation of Isoindoles by the Ring Contraction of 1-alkyl-1, 4-benzodiazepines," *Journal of Organic Chemistry,* (Mar. 1969) vol. 34, No. 3, pp. 649-654.

Berge, S.M., et al, "Pharmaceutical Salts," *Journal of Pharmaceutical Sciences,* (Jan. 1977) vol. 66, Issue 1, pp. 1-19.

Seivewright, N., et al., "Withdrawal Symptoms from High Does Benzodiazepines in Poly Drug Users,"*Drug and Alcohol Dependence,* (Mar. 1993) vol. 32 No. 1, pp. 15-23.

REGISTRY METHOD AND CONTROL SYSTEM FOR DEA SCHEDULE II-V MEDICINES

This application claims priority to U.S. provisional application No. 60/656,232, filed Feb. 24, 2005, the contents of which are hereby incorporated by reference in their entirety.

FIELD OF THE INVENTION

The present invention relates to compositions and methods for synthesizing labeled drugs. The present invention further relates to methods for preventing or stopping prescription drug abuse for all agents registered as a Drug Enforcement Agency (DEA) schedule II through schedule V medications. Further, the present invention provides methods for monitoring patient compliance with prescribed drug treatment. The present invention also provides methods for facilitating a replacement prescription when a patient is left without access to their prescribed drug. Furthermore, the present invention provides a method to improve employee compliance with an employer's drug policies via either a voluntary or compulsory system for enhanced drug testing.

BACKGROUND

Abuse of prescribed drugs such as benzodiazepines, amphetamines, amphetamine-like drugs, and opioid narcotics pose a major health risk and numerous enforcement problems in the United States and worldwide.

Benzodiazepines are anxiolytic (anxiety-relieving), hypnotic (sleep-inducing) and increase a patient's seizure threshold. Benzodiazepines are prescribed for medical conditions including anxiety, insomnia, alcohol withdrawal, seizures and as anesthetic agents given prior to and during surgery. The class of benzodiazepines contains many different medications. A partial list includes: midazolam (Versed), triazolam (Halcion), alprazolam (Xanax), lorazepam (Ativan), chlordiazepoxide (Librium), diazepam (Valium), bromazepam (Lexotan), flunitrazepam (Rohypnol, the "date-rape" drug), flurazepam (Dalmane), nitrazepam (Mogadon), oxazepam (Serenid), and temazepam (Restoril, Normison, Euhypnos). Benzodiazepines act on the central nervous system through interactions with gamma amino butyric acid (GABA) receptors. A physician, or para-professional, must hold a current and valid DEA certificate and be in good standing to prescribe a benzodiazepine. Benzodiazepines, while widely prescribed for a number of indications, are especially prone to substance abuse because they are rapidly acting anxiolytic agents.

The DEA recognizes the high propensity for abuse of benzodiazepines and has thus classified benzodiazepines as schedule IV medications. Benzodiazepine abusers often engage in "doctor-shopping," i.e., obtaining overlapping benzodiazepine prescriptions from different physicians. Doctors' prescriptions are the primary source of illicit benzodiazepines (Ashton H, Drugs and Dependence. 2002; 197-212 (Harwood Academic Publishers)). Benzodiazepines are often mixed with alcohol and commonly form part of a polysubstance abuse pattern, which can include heroin, opioids, cocaine and amphetamines (see Ashton). When benzodiazepines are mixed with alcohol, the intoxicating effects are not merely additive, but synergistic, and pose significant additional safety risks to individuals operating motor vehicles, passengers in their vehicles and those who share the road with them.

Amphetamines are used to treat medical conditions including Attention Deficit Disorder (ADD), Attention Deficit Hyperactivity Disorder (ADHD), narcolepsy, depression, and historically were used as appetite suppressants or weight loss medications. The family of compounds derived from amphetamine (Benzedrine) include dextroamphetamine (Dexedrine), methamphetamine (Desoxyn), benzphetamine (Didrex) and a number of others.

Methylphenidate (Ritalin) is an amphetamine-like drug prescribed for the treatment of the same disorders as amphetamines, perhaps with a somewhat lower probability of producing addictions. Both methylphenidate and its analogues, as well as the amphetamines and their analogues, are frequently prescribed to children and unfortunately are often used and abused by older siblings and others. On many college campuses, university students have found that crushing and snorting methylphenidate and amphetamines can produce cocaine-like euphoria.

Long-term, high dosage use of amphetamines and amphetamine-like drugs can result in symptoms of anxiety, panic, hallucinations and paranoia. Because these agents are sympathomimetic, they also act to increase heart rate, blood pressure and, at times, insomnia. Amphetamines and amphetamine-like drugs are extremely psychologically addictive because they increase brain dopamine levels and specifically target the brain's reward center, i.e., the nucleus accumbens.

A publication, Monitoring the Future Survey (MTF), funded by the National Institute on Drug Abuse, National Institutes of Health, and Department of Health and Human Services assesses the extent of drug use among adolescents and young adults in the United States. The 2003 MTF data on annual use indicate that 2.6% of 8th-graders abused Ritalin, as did 4.1% of 10th-graders and 4.0% of 12th-graders.

Opioids are commonly prescribed for their effective analgesic properties. Some of the medications that fall within this class include morphine, codeine, oxycodone (OxyContin), propoxyphene (Darvon), hydrocodone (Vicodin), hydromorphone (Dilaudid), and meperidine (Demerol). In addition to their pain-relieving properties, some of these drugs—for example, codeine and diphenoxylate (Lomotil)—can be used to relieve coughs and diarrhea. Long-term use of opioids can lead to physical dependence and addiction.

The methods of the present invention can stop or prevent prescription drug abuse because a patient is denied access to a second, overlapping prescription and doctor-shopping is effectively thwarted. Prevention of drug abuse can be especially beneficial to the individual and society because of the high rates of relapse following treatment for drug abuse. For example, the rate of relapse following benzodiazepine detoxification has been reported to be over 90 percent (Seivewright N and Dougal W. Drug Alcohol Depend. 1993; 32:15-23; Seivewright et al., Int J Drug Policy. 1993; 4:42-48).

Centralized databases for recording and monitoring prescription medications have been proposed, see, e.g., U.S. Pat. No. 6,687,676. Recordation in a database alone (without drug labeling) does not address the problems of abuse in which the abuser receives drug from a third party, unauthorized provider (e.g., a friend, a drug dealer), or an unscrupulous or unknowing provider (e.g., an unknowing doctor). Use of a database alone, would not allow a prescriber to discern whether the abuse is occurring due to medications supplied by a third party or unscrupulous/unknowing provider because medication from the two sources can not be differentiated. The methods of the present invention would allow identification of the source of the illicit medication because any unlabeled medication in the patient's tissue or body fluid is evidence of abuse.

SUMMARY OF THE INVENTION

The present invention relates to labeled drugs, methods for synthesizing labeled drugs and pharmaceutical compositions including labeled versions of DEA schedule II to V drugs. In aspects of the present invention, a labeled drug prescription is recorded in a registry. The present invention further relates to methods for preventing or stopping prescription drug abuse. Further, the present invention provides methods for monitoring patient compliance with prescribed drug treatment. The present invention also provides methods for facilitating replacement drug prescription when a patient is left without access to their prescribed drug.

In one embodiment, labeled benzodiazepines according to the present invention are represented by general Formula I as follows:

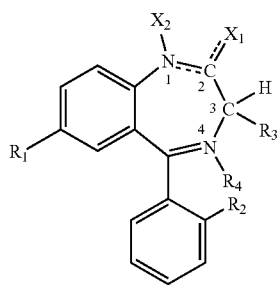

I wherein,

At least two of the atoms of the structure are present as isotopes $^2H$, $^{13}C$, $^{15}N$, or $^{18}O$;

$R_1$ is selected from chlorine, fluorine and nitro;

$R_2$ is selected from hydrogen, fluorine, or chlorine;

$R_3$ is selected from hydrogen, deuterium, carboxy (—COOH) or hydroxy;

$R_4$ is selected from no substituent or oxygen;

$X_1$ is selected from oxo, $^{18}$oxo, sulphur (=S) or aminomethyl (—NHCH$_3$);

$X_2$ is selected from no substituent, hydrogen, methyl, —CH$_2$CH$_2$N(CH$_2$CH$_3$)$_2$, trifluoroethyl (—CH$_2$CF$_3$), or methylenecyclopropyl

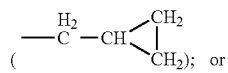

$X_1$ and $X_2$ together represent the bridge

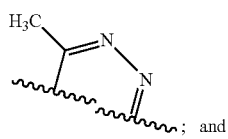
; and when $X_2$ is no substituent or $X_1$ is amino methyl (—NHCH$_3$), there is a double bond between nitrogen-1 and carbon-2 and a single bond between carbon-2 and $X_2$; and when $X_1$ is oxo or $^{18}$oxo, or $X_1$ and $X_2$ together represent the bridge

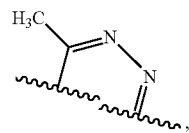
, there is a single bond between nitrogen-1 and carbon-2 and a double bond between carbon-2 and $X_2$;

and pharmaceutically acceptable salts and solvates, and mixtures thereof.

Labeled amphetamines according to the present invention are represented by general Formula II:

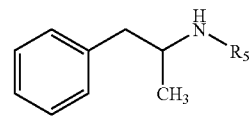

II wherein

At least one of the atoms of the structure are present as isotopes $^2H$, $^{13}C$ or $^{15}N$;

$R_5$ is selected from hydrogen or methyl; and pharmaceutically acceptable salts and solvates, and mixtures thereof.

More particularly, the present invention includes labeled amphetamines:

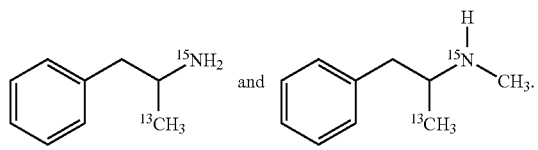

In another aspect, the present invention includes labeled methylphenidate according to the following structural formula (III):

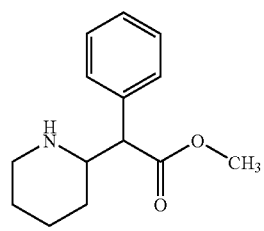

III wherein at least one of the atoms of the structure are present as isotopes $^2H$, $^{13}C$ or $^{15}N$; and pharmaceutically acceptable salts and solvates, and mixtures thereof.

In yet another aspect, the present invention includes labeled opiates according to structural formula IV:

IV wherein
at least one of the atoms of the structure are present as isotopes $^2$H, $^{13}$C, $^{15}$N, or $^{18}$O;
$R_1$ is selected from hydrogen, deuterium, —OH, or $^{18}$OH;
$R_2$ is selected from hydrogen or deuterium;
$R_3$ is selected from hydrogen or deuterium; or
$R_2$ and $R_3$ are not present and there is a C=C double bond between carbon 2 and carbon 3;
$R_4$ is selected from hydrogen or deuterium;
$R_5$ is selected from —OH or $^{18}$OH; or
$R_4$ and $R_5$ together form oxo (=O) or (=$^{18}$O);
$R_6$ is selected from H or CH$_3$; and
pharmaceutically acceptable salts and solvates, and mixtures thereof.

In yet another aspect, the present invention includes labeled methadone, wherein
the labeled methadone comprises at least one isotopic label independently selected from $^2$H, $^{13}$C, $^{15}$N, and $^{18}$O.

In yet another aspect, the present invention includes labeled fentanyl, wherein
the labeled fentanyl comprises at least two isotopic labels independently selected from $^2$H, $^{13}$C, $^{15}$N, and $^{18}$O.

In yet another aspect, the present invention includes labeled zolpidem, wherein
the labeled zolpidem comprises at least one isotopic label independently selected from $^2$H, $^{13}$C, and $^{15}$N, and
pharmaceutically acceptable salts thereof.

In yet another aspect, the present invention includes labeled buprenorphine, wherein
the labeled buprenorphine comprises at least one isotopic label independently selected from $^2$H, $^{13}$C, and $^{15}$N.

In yet another aspect, the present invention includes labeled tramadol, wherein
the labeled tramadol comprises at least one isotopic label independently selected from $^2$H, $^{13}$C, and $^{15}$N.

In one embodiment of the invention, a method for preventing drug abuse is provided wherein a prescriber identifies a patient as a potential abuser, prescribes a single, double, triple or higher multiple of a labeled drug to the potential abuser, records the prescription on a national registry, tests a tissue or body fluid (e.g., urine or blood) of the potential abuser for the presence of unlabeled drug, and identifies an abuser as an individual who tests positive for unlabeled drug.

In another embodiment of the invention, a method for monitoring compliance with prescribed drug treatment is provided wherein a prescriber prescribes a drug product in which one or more of the atoms has been replaced with a labeled atom. According to the invention, one, two, three or more atoms of a drug product may be replaced with a labeled atom to enable rapid identification of the product. In another embodiment, a drug product that has been labeled on two, three or more atoms is administered to a patient, the prescription is recorded on a national registry, and a tissue or body fluid (e.g., urine or blood) of the patient is thereafter tested for the presence of labeled and unlabeled drug. The test result identifies a non-compliant patient as an individual who tests negative for the prescribed labeled drug.

The present invention further provides a method in which a prescriber prescribes a drug that has been single, double or triple labeled and wherein the patient is unaware of the number of labels on the prescribed drug; the prescriber records the prescription in a registry; the patient is tested for the presence of unlabeled drug and labeled drugs having one, two, three or more labels; and a provider refuses to re-prescribe the drug to a patient testing positive for unlabeled drug or labeled drug having a number of labels different from the prescribed labeled drug.

The invention further comprises a method for prescribing a labeled controlled drug to a patient, which includes the steps of:

(a) creating a drug registry containing information on prescriptions written for controlled drugs and the identity of the patient receiving such prescriptions, (b) recording all controlled drug prescriptions in the registry, (c) interrogating the drug registry for information on the patient, and (d) prescribing a labeled controlled drug to a patient only if the patient does not have an unexpired prescription for the same controlled drug or another controlled drug of the same class (e.g., the controlled drug and the another controlled drug are both opioids) recorded in the registry.

In an embodiment of the invention, the results of a test on a patient's tissue or body fluid for the presence of labeled or unlabeled drug is recorded on the registry.

In another aspect of the present invention, a method is provided for prescribing a labeled controlled drug to a patient, which includes the steps of:

(a) creating a drug registry containing information on prescriptions written for controlled drugs and the identity of the patient receiving such prescriptions;

(b) recording all controlled drug prescriptions and patient identities in the registry, (c) interrogating the drug registry for information on the patient, (d) testing the patient's tissue or body fluid for the presence of labeled or unlabeled controlled drug, and (e) prescribing a labeled controlled drug to a patient only if the patient does not have:

(i) a positive test result for an unlabeled controlled drug or a labeled controlled drug that is not recorded on the registry, or (ii) an unexpired prescription for the same controlled drug recorded in the registry.

In a further aspect of the present invention, a method is provided for prescribing a labeled controlled drug to a patient, which includes the steps of:

(a) creating a drug registry containing information on prescriptions written for controlled drugs and the identity of the patient receiving such prescriptions, (b) recording all controlled drug prescriptions in the registry, (c) interrogating the drug registry for information on the patient, (d) comparing a prescription for a labeled controlled drug with the registry information on the patient; and (e) issuing the prescription only if the patient does not have an unexpired prescription for the same controlled drug recorded in the registry.

A drug can be labeled with a stable isotope according to the methods of the present invention by identifying suitable sites for isotope substitution such that substitution does not affect the activity of the drug. Following identification of a suitable substitution site(s), isotopes are substituted onto the drug by methods well known in the art as disclosed in, for example, Voges et al., Proceedings of the International Symposium, $5^{th}$ Strasbourg, June 20-24 (1995):1-26; and Mertel H, Drug Fate and Metabolism 1979; 3:133-191.

Synthesis of a labeled drug according to the methods of the present invention includes incorporation of isotopically labeled fragments of a drug that can be derived from commercially available reagents containing one or more heavy atom isotopic labels with greater than 90% isotopic purity. The isotopic labels are incorporated at metabolically stable sites of the drug so that they are retained on the compound while it is in the tissues or body fluids of a patient (e.g., the labels are retained on the compound when the compound is in the blood stream or when it passes from the body in the urine). Stable isotope labels 2H, 13C, 15N, 17O, 18O, 33S, 34S, and 36S are preferred. Especially preferred stable isotope labels are 13C, 15N, 17O and 18O. The cost of synthesizing labeled drugs according to the present invention can be contained by selecting drugs, which are dosed in small amounts of active agent (i.e., less than 250 mg). Cost can further be contained by the economies of scale involved when large amounts of labeled drug are produced.

The present invention provides a method for identifying a non-compliant patient who does not comply with a prescription for medication, which includes the steps of:

(a) prescribing a medication to a patient for a period of time comprising a first predetermined interval and a second predetermined interval wherein the first predetermined interval and second predetermined interval are consecutive;

(b) providing the patient with a supply of the medication adequate to cover the period to time, wherein the supply comprises units of the medication having a plurality of different labels;

(c) instructing the patient to self-administer the labeled units having a first label during the first predetermined time;

(d) instructing the patient to self-administer the labeled units having a second label during the second predetermined time, the second label being different from the first label;

(e) testing the patient for the presence of the first label during the second predetermined interval;

(f) testing the patient for the presence of the second label during the second predetermined interval; and (g) identifying a patient testing negative for the presence of the first label and the second label as non-compliant with the prescription medication for the period of time.

In a preferred embodiment, the period of time is about one month.

DETAILED DESCRIPTION

Definitions

Figure 1:
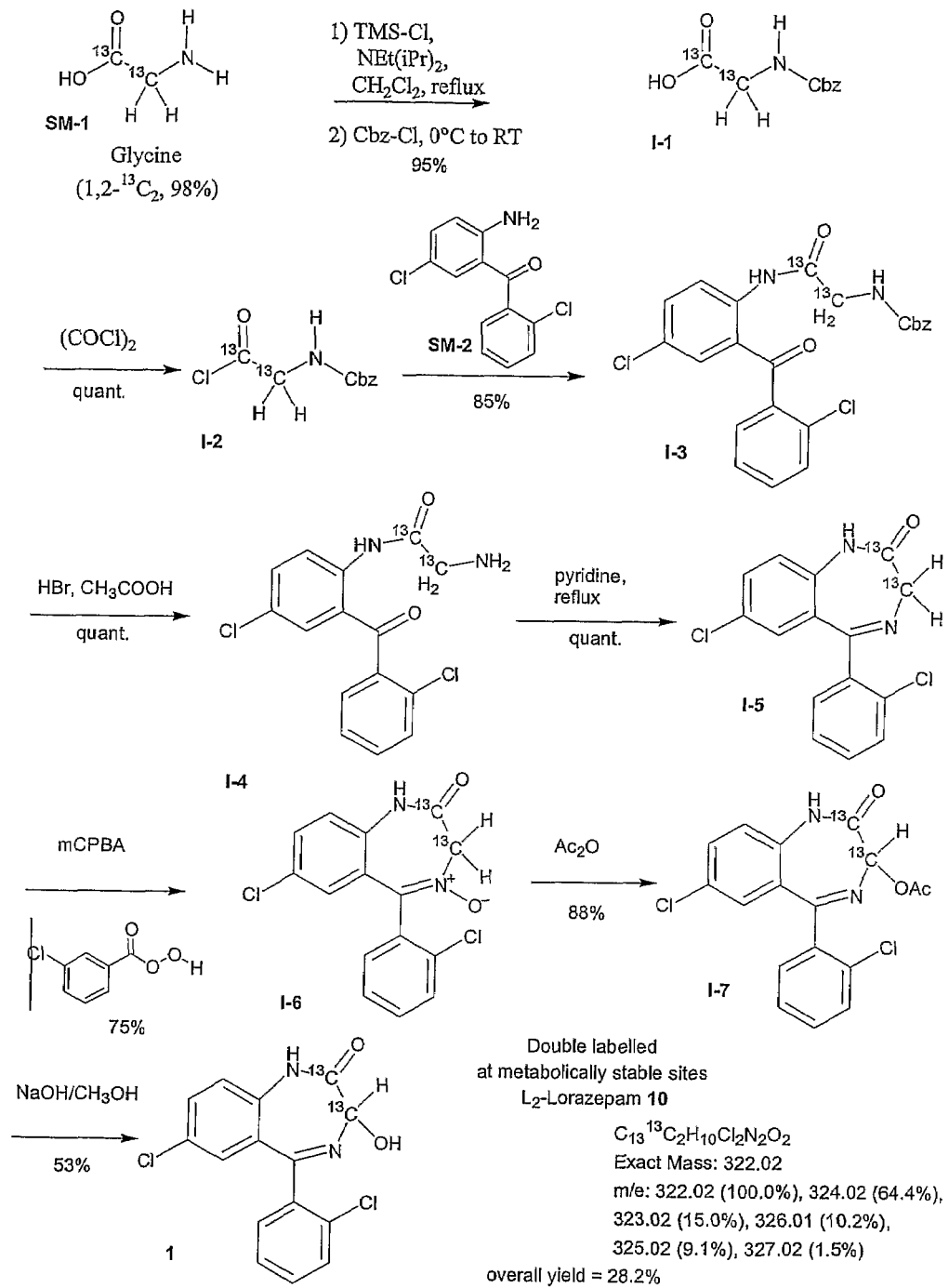
FIG. 1 shows the synthetic pathway for double isotope labeled lorazepam.

As used herein, "drug," "schedule drug," "controlled drug," "controlled pharmaceutical agent" or "controlled substance" refers to a prescribed medication having the potential for abuse (i.e., a DEA schedule II through V medication). A drug according to the present invention includes, for example, medications in the benzodiazepine, amphetamine, amphetamine-like, and opioid classes.

As used herein, "label" refers to a tag or marker that is added onto or made part of the molecular structure of a drug, which permits a labeled drug to be distinguished from an unlabeled drug in an individual's tissue or body fluid but does not affect the pharmacologic activity of the drug. A preferred label according to the present invention is a stable isotope.

A "labeled drug" as used herein refers to a drug having at least one label (e.g., single or double isotope labeled diazepam) or a mixture of a drug having different labels in a specified ratio (e.g., a mixture of single labeled diazepam and double labeled diazepam in a 9:1 ratio).

As used herein, the term "abuse" refers to use of a drug (e.g., a benzodiazepine) in a greater than prescribed amount or frequency. An "abuser" is an individual who abuses a drug.

A "provider," as used herein is a doctor or anyone legally authorized to prescribe a drug, e.g., a benzodiazepine.

A "prescriber," as the term is used herein, is a provider who has written a prescription for a drug, e.g., a benzodiazepine, for a particular patient.

Labeled Drugs

According to the present invention, a drug is labeled so that it can be identified when a specimen of a tissue or body fluid is removed from a patient receiving the labeled drug (i.e., by assaying in a sample of the patient's tissue or body fluid) and readily distinguished from an unlabeled version of the same drug. More particularly, the drug is labeled to contain an isotopic label(s) at a metabolically stable position(s) such that the labeled drug has the same biological effects as unlabeled drug. The isotopes according to the present invention are stable and inert. Preferably, the isotopes are rare. Isotopes according to the present invention include isotopes of hydrogen, carbon, nitrogen, oxygen, and sulfur (e.g., 2H, 13C, 15N, 17O and 18O).

A labeled drug according to the present invention can be selected and synthesized by a method, which includes the steps of:

(a) selecting a drug that is medicinally useful but can be abused (i.e.: any of the schedule II through V drugs);

(b) selecting atoms in the drug compound that are metabolically stable, i.e., atoms that are retained in the drug compound when the drug is in the blood stream and urine;

(c) selecting a known synthesis for the drug that includes reagents that allow the addition of non-radioactive isotope labels at an intermediate step in the synthesis;

(d) adding the labeled reagent;

wherein a labeled drug is synthesized.

Introduction of the label late in the synthesis is more cost effective than introduction of the label early in the synthesis of the labeled drug.

The isotope labels should be inserted with high fidelity (about 90% or greater). Preferably, the isotopically labeled reagents are commercially available with high purity of the isotope label. Isotopically labeled reagents containing 2H, 13C, 15N, 17O, and 18O are preferred. One isotope label in a drug can be used according to the present invention. More than one isotope label in a drug is preferred because the mass signature of the labeled drug will be more distinct for a drug with more than one label compared to a drug with one label.

Different labeled versions of the same drug can be mixed together to create uniquely identifiable mixtures. Thus, a very large number of uniquely identifiable isotope formulations can be created. For example, singly labeled oxycodone can be mixed at a 9:1 ratio with doubly labeled oxycodone, this would provide a mass signature in a drug test that would make this 9:1 mixture distinguishable from an 8:2 or 7:3 mixture. The only limit to the number of uniquely identifiable labeled formulations is the precision to which mass spectrometry can distinguish between isotope mixtures. The ratio of the labeled versions of a drug can be used as a code in conjunction with the national registry system that is part of the present invention.

The present invention provides labeled drugs and methods for synthesizing labeled drugs. A preferred label is a stable isotope. In an embodiment of the invention, it is advantageous to include at least one isotope label in a drug. The inclusion of isotopes in a drug increases the cost of synthesis, which can discourage the production of labeled illicit or "street" drugs.

Preferred labeled drugs according to the present invention are labeled drugs in the benzodiazepine, amphetamine, amphetamine-like (e.g., methylphenidate), and opioid class.

Registering a Labeled Drug

A registry according to the present invention is a database accessible to providers of drugs wherein data relating to the prescription of a labeled drug can be recorded and accessed by a provider or pharmacist. The registry includes a host system capable of selectively receiving, storing and dispensing prescription information; and a plurality of provider systems remote from the host system, which are capable of receiving and inputting prescription information into the host system. The provider system is also capable of retrieving prescription information from the host system. The registry can be accessed, for example, using a public telephone line with a coded connection (e.g., a password). The registry is constructed to protect patient privacy and is preferably compliant with existing law relating to patient privacy and right of access (e.g., Health Insurance Portability and Accountability Act ("HIPAA")). Access to a registry according to the present invention is limited to providers and, optionally, pharmacists, as well as any other individuals authorized by law (e.g., law enforcement officers). Methods for ensuring privacy are well known and include, for example, providing unique patient identifiers. For example, when a patient enters the registry he is assigned a unique identifying number or alphanumeric code that can be used to uniquely identify him and to distinguish him from other registry participants. Construction and maintenance of a registry according to the present invention is well known as provided in, for example, U.S. Pat. No. 6,687,676.

The data required to be entered by a prescriber is preferably kept to a minimum to encourage provider compliance. Such minimum data includes a patient's name or identifier, a prescriber's name or identifier, the start date of the prescription (i.e., the date the drug is dispensed), the drug prescribed, the dosage and frequency, duration of treatment, and the indication for the prescription. In an embodiment of the invention, a patient would have to show a provider, as well as a pharmacist, a valid state or federal form of identification in order to obtain and fill a prescription. Additional forms of identification can include, for example, unique identifiers such as fingerprints, retinal scans, DNA fingerprinting or other biometric identifiers. A unique identifier decreases the likelihood of a patient submitting multiple identities within the registry system.

Any physician can interrogate the registry in order to determine if a new patient had previously received a prescription form another doctor for the same DEA schedule II to V drug. The interrogation can be via the patient's number or through use of the patient's assigned "identifier" or password on the system.

In an embodiment of the present invention, a pharmacist can access the registry, and a labeled drug prescription will not be filled and dispensed unless the prescription has been recorded in the registry.

In another embodiment of the present invention, a pharmacist can access the registry, and a labeled drug prescription will not be dispensed for a patient if a current labeled drug prescription for the patient appears in the registry. According to this aspect of the present invention, concurrent dispensing of the same or similar drugs can be prevented.

In another aspect of the present invention, a pharmacist can access the registry and record in the registry the date, and optionally the time, when a drug prescription is being filled. This will "start the clock" on the prescription Detecting a Labeled Drug An isotopically labeled drug can be detected and distinguished from an unlabeled drug by any method, which can detect labeled and/or unlabeled drug in an individual's tissue or body fluid (e.g., blood or urine) and distinguish the molecular weight of the labeled and unlabeled drug. In an aspect of the invention, a detection method can distinguish drugs having different labels (e.g., one isotope label versus two isotope labels versus three isotope labels). In another aspect of the invention, a detection method can distinguish drugs containing different mixtures of labels (e.g., a 9:1 mixture of singly and doubly labeled oxycondone versus a 1:1 mixture of singly and doubly labeled oxycondone).

A labeled drug can be distinguished from unlabeled drug by, for example, mass spectrometry, nuclear magnetic resonance, gas chromatography/mass spectrometry (GC/MS), and liquid chromatography/mass spectrometry (LC/MS).

Detection of labeled and unlabeled drugs using GC/MS or LC/MS would be carried out on a sample of a few milliliters of blood or urine or some other matrix such as sweat, saliva, meconium, or a nail. Prior to GC/MS or LC/MS a sample preparation step is often carried out that may involve cleavage of conjugates, isolation, and derivatization, preceded or followed by cleanup steps. After the sample preparation step, an isolation step involving liquid-liquid extraction (LLE) or by solid-phase extraction (SPE) is carried out to extract the organic components from the prepared sample. One method of extraction is to insert a Twister™ stir bar into the prepared liquid sample and stir for a few minutes. The stir bar is removed, washed with water, dried and heated to volatilize the organics. The volatile organic compounds are injected into a GC/MS and run for about 30 minutes.

Gas chromatography (GC) separates drugs in a sample by passing the sample through a column with a stream of helium gas. The inside surface of the column is coated with wax. The wax slows down the drugs as they pass through the column so that some drugs take longer than others to reach the end of the column. As the drugs exit the column, the mass spectrum detector records the fragmentation fingerprint of the drugs. Drug identification is based on its transit time through the column and molecular fragmentation fingerprint. These two unique characteristics provide precise identification (See Forensic Applications of Mass Spectrometry, by Jehuda Yinon ISBN: 0849382521; Advances in Forensic Applications of Mass Spectrometry, by Jehuda Yinon, ISBN: 0849315220).

Labeled and unlabeled drug emerge from the gas chromatograph at the same time, but are distinguishable by mass spectroscopy. For example, the mass of unlabeled alprazolam ("rA") is 308 Daltons. Using the technique of gas chromatography-mass spectrometry, unlabeled alprazolam is detected as a mass envelope of m/e: 308.08 (100.0%), 310.08 (32.2%), 309.09 (18.5%), 311.08 (6.4%), 310.09 (1.6%), 309.08 (1.5%). Under the same conditions, singly labeled alprazolam is detected with the same retention time as unlabeled alprazolam but with a mass envelope of m/e: 309.09 (100.0%), 311.09 (32.2%), 310.09 (19.9%), 312.09 (6.0%), 311.10 (1.6%). The fragment of labeled alprazolam will be detected with the largest peak at m/e 274.11. If LC/MS is used to detect rA, under acidic conditions rA will be detected in the protonated form and the m/e envelope will be shifted up by one mass unit (m+1)/e: 309.09 (100.0%), 311.09 (32.2%), 310.09 (19.9%), 312.09 (6.0%), 311.10 (1.6%). Under these same conditions, singly-labeled alprazolam will also be shifted by one mass unit (m+1)/e: 310.09 (100.0%), 312.09 (32.2%), 311.09 (19.9%), 313.09 (6.0%), 312.10 (1.6%). These small differences in mass are easily distinguished by mass spectrometry.

A labeled drug according to the present invention contains one or more stable isotopes. A stable isotope includes, for example, hydrogen 2(2H), carbon 13 (13C), nitrogen 15 (15N), oxygen 17 (17O), oxygen 18 (18O), sulphur 33 (33S), sulphur (34S), sulphur 36 (36S). Stable isotopes of other elements such as chlorine and bromine can also be used but they are less commonly found in drugs of abuse. The compositions and methods of the present invention provide for substitution of hydrogen (1H) with 2H, carbon (12C) with 13C, nitrogen (14N) with 15N, and oxygen (16O) with 17O or 18O, and sulphur (32S) with 33S or 34S or 36S, such that a drug is labeled at metabolically stable sites.

A labeled drug according to the present invention can also contain mixtures of labeled drug containing two or more different labeled versions of the same drug in a specified ratio (e.g., a mixture of single and double labeled drug in a ratio of 2:1).

Methods of Preventing or Stopping Drug Abuse

According to the present invention, drug abuse can be prevented by prescribing a labeled drug to a patient; recording a patient identifier and the labeled drug prescription in a registry accessible to providers; testing a fluid or tissue sample from the patient for the presence of unlabeled drug or isotopically labeled drug containing a different number of isotopic labels than was originally prescribed. These patients would be identified as being non-compliant with their responsibility to take only medication prescribed by a single provider. Options such as detoxification and drug treatment could at that point be offered.

In an aspect of the present invention, a patient can be identified as non-compliant if the patient is tested and a mixture of labeled drug is identified in the patient's tissues that is different than the formulation that the patient was prescribed.

In an example according to the present invention, a doctor (i.e., a prescriber) prescribes a labeled drug (e.g., triple-isotope labeled diazepam) to a patient for the treatment of a medical condition (e.g., alcohol withdrawal). In an embodiment of the invention, a prescriber can select a labeled drug from among a group of the same drug having different labels (e.g., single- or double-isotope labeled diazepam); according to this embodiment, the particular label selected is not disclosed to the patient. Further, according to the invention, the doctor or his staff records the labeled drug prescription in a registry by accessing the registry using, for example, a personal computer in the doctor's office. The data included in the recordation includes, for example, the patient's name or unique identifier, the doctor's name, the prescribed drug, the date of the prescription, the dosage, frequency and duration of treatment, and the medical indication for the prescription. In an embodiment of the invention, a pharmacist accesses the registry to confirm recordation of the prescription prior to dispensing the drug.

In an embodiment of the present invention, the dispensing of isotopically labeled medication, whether it be singly, doubly or multiply labeled moieties, can be double-blind with respect to the prescribers as well as the patients. Such double-blind dispensing can prevent unscrupulous providers from intentionally colluding with patients to receive medication outside of the registry system.

In an aspect of the present invention, an employer having an employee's consent can ensure that the employee is receiving a prescription drug as prescribed by using the registry system. By using only isotopically labeled medication, the employer can know with certainty that an employee is only receiving the medication in the intended quantities. This would prevent an employee who revealed that he is taking a medication from receiving quantities of that medication beyond the scope of what the prescriber of the medication intends.

Further, according to the invention, insurance companies or third party payers can be ensured that the individual who is covered by the policy is only receiving schedule drug within the purview of the registry. This would allow an insurer to investigate whether a schedule drug could be exacerbating or disguising an underlying medical condition via overuse of the prescribed agent.

Further, according to the invention, if the patient visits the same doctor or another doctor (a provider, but not the prescriber) seeking a prescription for a drug that they are currently being prescribed, or a similar drug (e.g: if they are currently taking labeled oxycontin the prescriber may want to avoid prescribing additional opiates), the doctor (either the non-prescribing provider or the prescriber) can access the registry and determine the patient's eligibility to receive the requested drug. According to an embodiment of the invention, the doctor refuses to write a prescription for the drug if a current, filled prescription for the labeled drug is recorded in the registry. In another embodiment of the invention, the doctor tests the patient for unlabeled and labeled drug, and refuses to write a prescription for the patient with a recorded prescription for labeled drug who tests positive for unlabeled drug. In a further embodiment, a provider refuses to write a prescription for a drug if the patient tests positive for a labeled drug (e.g., triple-isotope labeled diazepam) different from the recorded prescribed labeled drug (e.g., double-isotope labeled diazepam).

Methods of Monitoring Patient Compliance

According to the present invention, a patient can be monitored for compliance with prescribed drug treatment by prescribing a labeled drug to a patient; recording the labeled drug prescription in a registry accessible to providers; testing a fluid or tissue sample from the patient for the presence of labeled and unlabeled drug; and identifying as non-compliant a patient testing negative for labeled drug. This can prevent an individual from registering with the database, not take the prescribed medication, and furnish the prescribed medication to a third party.

In an example, according to the present invention, a doctor (i.e., a prescriber) prescribes a labeled drug (e.g., triple-isotope labeled diazepam) to a patient for the treatment of a medical condition (e.g., alcohol withdrawal). In an embodiment of the invention, a prescriber can select a labeled drug from among a group of the same drug having different labels (e.g., single- or double-isotope labeled diazepam). According to this embodiment, the particular label selected is not disclosed to the patient. Further, according to the invention, the doctor or his staff records the labeled drug prescription in a registry by accessing the registry using, for example, a personal computer in the doctor's office. The data included in the recordation includes, for example, the patient's name or unique identifier, the doctor's name, the prescribed drug, the date of the prescription, the dosage, frequency, the duration of treatment, and the medical indication for the prescription. In an embodiment of the invention, a pharmacist accesses the registry to confirm recordation of the prescription prior to dispensing the drug.

Further, according to the invention, the patient visits the same doctor or another doctor (a provider, but not the prescriber). The doctor (either the non-prescribing provider or the prescriber) accesses the registry and tests the patient for unlabeled and labeled drug. The patient is identified as non-compliant if the patient tests negative for the recorded labeled drug.

Methods for Facilitating Replacement Drug Prescriptions

It is not uncommon for patients with prescribed drugs to be left without access to their prescription drugs and in need of a replacement prescription from a provider who was not the prescriber. For example, a traveler who forgot to pack his prescription drug can be on a trip far from home without a means of contacting his prescriber. In such situations, the traveler can visit a provider who was not the prescriber to obtain a replacement prescription. The provider may be reluctant to write such a prescription because of the possibility that the traveler is doctor-shopping.

The present invention provides a method for facilitating replacement drug prescription by a provider. According to the invention, the provider can access a registry and prescribe a replacement drug prescription to a patient with a current labeled drug prescription recorded on the registry in the situation where the labeled drug prescribed and recorded in the registry is not immediately available to the patient.

Methods for Safely Tapering a Drug

The present invention provides a method for safely tapering a drug. For example, a patient who is addicted to a drug (e.g., diazepam) sees a provider. The provider prescribes a tapering dosage regimen of labeled drug. For example, a patient would be dispensed a one week supply of isotopically labeled diazepam 10 mg per day, followed by a one week supply of isotopically labeled diazepam 7.5 mg per day, followed by a one week supply of isotopically labeled diazepam 5.0 mg per day and then a final one week supply of isotopically labeled diazepam 2.5 mg per day before the patient has been safely tapered from this dependency-inducing medication. To ensure compliance, a national database would contain a description of the patient's tapering regimen. According to the present invention, each dosage of drug in the regimen has a different label (e.g., the 10 mg diazepam is triple isotope labeled and the 5 mg diazepam is double isotope labeled). During the course of the taper regimen the tissue or body fluid of the patient is tested for labeled and unlabeled drug. A positive test for the labeled drug corresponding to the appropriate drug in the taper regimen at the time of testing indicates that the patient is properly adhering to the taper regimen (e.g., the patient tests positive for triple isotope labeled diazepam on a day when he should be taking triple labeled diazepam). A positive test for an unlabeled drug or a labeled drug that should not be present in the patient's tissue or body fluid at the time of the test indicates that the patient is not properly adhering to the taper regimen (e.g., the patient tests positive for double labeled diazepam on a day when he should be taking triple labeled diazepam). A negative test for labeled drug during the course of the taper regimen is another indication that the patient is not adhering to the taper regimen.

Also, according to the present invention, a more gradual taper can be achieved by mixing differently labeled drugs (e.g., a double labeled drug with a triple labeled drug) at different ratios (e.g., 9:1, 8:2, 7:3, . . . , 1.1, . . . 9:1) while at the same time steadily decreasing the total amount of drug in each dose. During the course of the taper regimen the tissue or body fluid of the patient is tested for the two labeled drugs. A positive test corresponding to the proper ratio of the two labeled drugs in the specimen indicates that the patient is properly adhering to the taper regimen (e.g., the patient tests positive for 80% triple isotope labeled diazepam and 20% double isotope labeled diazepam on a day when he should be 80% of the way through the taper regimen). A positive test for an unlabeled drug or a labeled drug that should not be present in the patient's tissue or body fluid at the time of the test indicates that the patient is not properly adhering to the taper regimen (e.g., the patient tests positive for double labeled diazepam on a day when he should be taking triple labeled diazepam). A negative test for labeled drug during the course of the taper regimen is another indication that the patient is not adhering to the taper regimen.

Methods for Identifying a Patient who is Non-Compliant with a Prescription for Medication The present invention provides a method for identifying a non-compliant patient who does not comply with a prescription for medication. According to this method, for example, a patient is prescribed a one month supply (a "period of time") of a medication. The one month supply of medication includes, for example, a three week supply of medication units having one isotopic label per unit and a one week supply of medication units having two isotopic labels per unit. The patient is instructed to self-administer the one label units for the first three weeks of the one month (a "first predetermined interval") and the two label units for the fourth week on the one month (a "second predetermined interval"). At any point during the fourth week, the patient is tested for the presence of the one label unit and the two label unit. A negative test for the one label unit identifies a patient who was non-compliant with the prescription during the first three weeks of the month. A negative test for the two label unit identifies a patient who was non-compliant during the fourth week of the month. A negative test for both the one label unit and the two label unit identifies a patient who was non-compliant with the prescription during the first three weeks of the month and the fourth week of the month. According to this method, the labeled medication administered during the first predetermined interval must have a half-life sufficiently long to remain at detectable levels in a patient during the second predetermined interval.

Salts, Solvates, Prodrugs, and Stereoisomers

Typically, a pharmaceutically acceptable salt of a compound of the present invention can be readily prepared by using a desired acid or base as appropriate. The salt may precipitate from solution and be collected by filtration or may be recovered by evaporation of the solvent. For example, an aqueous solution of an acid such as hydrochloric acid may be added to an aqueous suspension of a compound of the present invention and the resulting mixture evaporated to dryness (lyophilized) to obtain the acid addition salt as a solid. Alternatively, a compound of the present invention may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

The acid addition salts of a compound of the present invention can be prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

As used herein, the term "salts" can include acid addition salts or addition salts of free bases. Examples of acids which may be employed to form pharmaceutically acceptable acid addition salts include but are not limited to salts derived from nontoxic inorganic acids such as nitric, phosphoric, sulfuric, or hydrobromic, hydroiodic, hydrofluoric, phosphorous, as well as salts derived from nontoxic organic acids such as aliphatic mono- and dicarboxylic acids, phenyl-substituted alkanoic acids, hydroxyl alkanoic acids, alkanedioic acids, aromatic acids, aliphatic and aromatic sulfonic acids, and acetic, maleic, succinic, or citric acids. Non-limiting examples of such salts include napadisylate, besylate, sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M. et al. "Pharmaceutical Salts," J. of Pharma. Sci., 1977; 66:1).

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The salts of a compound of the present invention can form solvates (e.g. hydrates) and the invention also includes all such solvates.

The present invention also encompasses prodrugs of the aforementioned compounds of the present invention, i.e., compounds which release an active parent drug according to the aforementioned compounds in vivo when administered to a mammalian subject. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulflhydryl and amine functional groups of a compound of the present invention. Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

A compound of the present invention can exist in numerous forms of structural isomers that may be formed as a result of tautomerism, and may exist in different ratios at equilibrium. Due to dynamic equilibrium such isomers (tautomers) are rapidly interconvertible from one isomeric form to another. The most common isomerism is keto-enol tautomerism, but equilibrium between open chain and cyclic forms are also known. It is to be understood that whenever in the present invention we refer to aforementioned compounds of the present invention, we mean to include tautomeric forms thereof, keto-enol tautomeric, open chain-cyclic, isolated as separate isomers or existing in any other mixture of different ratios at equilibrium. The isomeric forms predominant for a particular compound of the present invention are dependent on the nature of the substituent, whether the compound exists in the free form or in the form of any of its salts, type of the salt, solvent in which the compound is dissolved, as well as pH value of the solution.

Compounds of the present invention may further exist as different geometric isomers or different stereoisomers. Isomers that differ only with regard to the arrangement of the atoms in the space around the asymmetric (stereogenic, chiral) center are called "stereoisomers". Stereoisomers that are not mirror images of each other are called diastereomers, while stereoisomers that have a mirror-image relationship, i.e. that are mirror images of each other, are called enantiomers. Each stereoisomer may be characterized by determining the absolute configuration of the stereogenic center by the use of Cahn-Ingold-Prelog priority rules and hence characterized as the R- or S-isomer. Another way of identification of stereoisomers is the measurement of the rotation of the plane of polarized light that passes through the molecule, and designating chiral molecules to be right-rotating (+) or left-rotating (−) isomers. Chiral molecules may exist in a form of single enantiomer or in a mixture of enantiomers. A mixture consisting of equal parts (+) and (−) enantiomers of a chiral substance is called racemic mixture. The present invention relates to each stereoisomer that may be shown by the aforementioned compounds of the present invention either isolated as separate enantiomers, diastereomers or existing in racemic or any other mixture thereof.

Methods for determination of stereochemical configuration, resolution and separation of stereoisomers are well known from the literature. The enantiomers may be resolved by methods known to those skilled in the art, for example by formation of diastereomeric salts which may be separated, for example, by crystallization; formation of diastereomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. The diastereomeric pairs may be separated by methods known to those skilled in the art, for example chromatography or crystallization and the individual enantiomers within each pair may be separated as described above.

The present invention also encompasses stereoisomers of the syn-anti type, and mixtures thereof encountered when an oxime or similar group is present. The group of highest Cahn-Ingold-Prelog priority attached to one of the terminal doubly bonded atoms of the oxime, is compared with hydroxy group of the oxime. The stereoisomer is designated as Z (zusammen=together) or Syn if the oxime hydroxyl lies on the same side of a reference plane passing through the C=N double bond as the group of highest priority; the other stereoisomer is designated as E (entgegen=opposite) or Anti.

Compounds of the present invention may be in crystalline or amorphous form. Furthermore, some of the crystalline forms of the aforementioned compounds of the present invention may exist as polymorphs, which are included in the present invention.

Pharmaceutical Compositions

While it is possible that, for use in therapy, a compound of the invention may be administered as the raw chemical, it is preferable to present the active ingredient in a pharmaceutical formulation, e.g., when the agent is in admixture with a suitable pharmaceutical excipient, diluent or carrier selected with regard to the intended route of administration and standard pharmaceutical practice.

Accordingly, in one aspect, the present invention provides a pharmaceutical composition or formulation comprising at least one compound of the invention or a pharmaceutically acceptable derivative thereof in association with a pharmaceutically acceptable excipient, diluent and/or carrier. The excipient, diluent and/or carrier must be "acceptable" in the sense of being compatible with the other ingredients in the formulation and not deleterious to the recipient thereof.

The term "pharmaceutically acceptable", as used in connection with compositions of the invention, refers to molecular entities and other ingredients of such compositions that are physiologically tolerable and do not typically produce untoward reactions when administered to a mammal (e.g., human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The term "carrier" applied to pharmaceutical compositions of the invention refers to a diluent, excipient, or vehicle with which an active compound is administered. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. However, since benzodiazulene salt are highly soluble, aqueous solutions are preferred. Suitable pharmaceutical carriers are described in "Remington's Pharmaceutical Sciences" by E. W. Martin, 18th Edition. Particularly preferred for the present invention are carriers suitable for immediate-release, i.e., release of most or all of the active ingredient over a short period of time, such as 60 minutes or less, and make rapid absorption of the drug possible.

The term "pharmaceutically acceptable derivative" as used herein means any pharmaceutically acceptable salt, solvate or prodrug, e.g. ester, of a compound of the invention, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5th Edition, Vol 1: Principles and Practice, which is incorporated herein by reference to the extent of teaching such derivatives. Preferred pharmaceutically acceptable derivatives are salts, solvates, esters, carbamates and phosphate esters. Particularly preferred pharmaceutically acceptable derivatives are salts, solvates and esters. Most preferred pharmaceutically acceptable derivatives are salts and esters.

The compounds of the invention may be formulated for administration in any convenient way for use in human or veterinary medicine and the invention therefore includes within its scope pharmaceutical compositions comprising a compound of the invention adapted for use in human or veterinary medicine. Such compositions may be presented for use in a conventional manner with the aid of one or more suitable excipients, diluents and/or carriers. Acceptable excipients, diluents and carriers for therapeutic use are well known in the pharmaceutical art, and are described, for example, in Remington's Pharmaceutical Sciences, Mack Publishing Co. (A. R. Gennaro edit. 1985). The choice of pharmaceutical excipient, diluent and/or carrier can be selected with regard to the intended route of administration and standard pharmaceutical practice. The pharmaceutical compositions may comprise as—or in addition to—the excipient, diluent and/or carrier any suitable binder(s), lubricant(s), suspending agent(s), coating agent(s), solubilizing agent(s).

Preservatives, stabilizers, dyes and even flavoring agents may be provided in the pharmaceutical composition. Examples of preservatives include sodium benzoate, ascorbic acid and esters of p-hydroxybenzoic acid. Antioxidants and suspending agents may be also used.

For some embodiments, the agents of the present invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubilizer. Alpha-, beta- and gamma-cyclodextrins are most commonly used and suitable examples are described in WO 91/11172, WO 94/02518 and WO 98/55148.

The compounds of the invention may be milled using known milling procedures such as wet milling to obtain a particle size appropriate for tablet formation and for other formulation types. Finely divided (nanoparticulate) preparations of the compounds of the invention may be prepared by processes known in the art, for example see International Patent Application No. WO 02/00196 (SmithKline Beecham).

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia.

Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

The compounds of the invention may also be used in combination with other therapeutic agents. The invention thus provides, in a further aspect, a combination comprising a compound of the invention or a pharmaceutically acceptable derivative thereof together with a further therapeutic agent. The combinations may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations by any convenient route.

When administration is sequential, either the compound of the invention or the second therapeutic agent may be administered first. When administration is simultaneous, the combination may be administered either in the same or different pharmaceutical composition.

When combined in the same formulation it will be appreciated that the two compounds must be stable and compatible with each other and the other components of formulation. When formulated separately they may be provided in any convenient formulation, conveniently in such manner as are known for such compounds in the art.

The compositions may contain from 0.01-99% of the active material.

The preparation of pharmaceutical formulations may include blending, granulating, tabletting and dissolving the ingredients. Pharmaceutically acceptable carriers (binders and fillers) may be solid or liquid. Solid carriers may be lactose, sucrose, talcum, gelatine, agar, pectin, magnesium stearate, fatty acids etc. Liquid carriers may be syrups, oils such as olive oil, sunflower oil or soy bean oil, water etc. Similarly, the pharmaceutically acceptable Formulations may also contain a component for a sustained release of the active component such as e.g. glyceryl monostearate or glyceryl distearate.

Dosages

The dosage of a labeled drug according to the present invention is the same as the dosage of the corresponding unlabeled drug, e.g., labeled diazepam according to the present invention is dosed in the same amount and frequency as unlabeled diazepam.

Typically, a physician will determine the actual dosage which will be most suitable for an individual subject. The specific dose level and frequency of dosage for any particular individual may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The daily dosage level of the agent may be in single or divided doses.

Methods of Synthesizing a Labeled Drug

It will be appreciated by those skilled in the art that it may be desirable to use protected derivatives of intermediates used in the preparation of the compounds of Formulae I-IV. Protection and deprotection of functional groups may be performed by methods known in the art. Hydroxyl or amino groups may be protected with any hydroxyl or amino protecting group, for example, as described in Green T. W.; Wuts P. G. M. *Protective Groups in Organic Synthesis*: John Wiley and Sons, New York, 1999. The amino protecting groups may be removed by conventional techniques. For example, acyl groups, such as alkanoyl, alkoxycarbonyl and aryloyl groups, may be removed by solvolysis, e.g., by hydrolysis under acidic or basic conditions. Arylmethoxycarbonyl groups (e.g., benzyloxycarbonyl) may be cleaved by hydrogenolysis in the presence of a catalyst such as palladium-on-charcoal.

The synthesis of the target compound is completed by removing any protecting groups, which are present in the penultimate intermediate using standard techniques, which are well known to those skilled in the art. The deprotected final product is then purified, as necessary, using standard techniques such as silica gel chromatography, HPLC on silica gel, and the like or by recrystallization.

Synthesis of Labeled Benzodiazepines

Compounds of Formula I and pharmaceutically acceptable derivatives thereof may be prepared by the general methods outlined hereinafter, said methods constituting a further aspect of the invention. In the following description, the groups $R_1$ to $R_4$, $X_1$, $X_2$ have the meaning defined for the compounds of Formula I unless otherwise stated.

A further object of the present invention relates to the preparation of compounds of Formula I according to processes comprising:

(a) For compounds of Formula I, wherein there is a C—N single bond between nitrogen 1 and carbon 2, $X_1$ is oxygen and there is a C=O double bond between $X_1$ and carbon 2, and $X_2$ is hydrogen and $R_3$ is hydrogen and $R_4$ is no substituent:

condensing of a compound of Formula B1:

B1 wherein
the compound B1 can contain from zero to at least one isotopic labels;
R1 is selected from chlorine, fluorine or nitro; and
R2 is selected from hydrogen, fluorine, or chlorine,
with an isotopically labeled compound B2

B2 wherein
at least one atom labeled with "*" is a stable isotope such as $^{13}C$ for C, $^{15}N$ for N, $^{18}O$ for O and $^{2}H$ for H;
Y is a leaving group such as chloro, fluoro, or substituted phenyl alkoxide;
P1 is an amine protecting group,
then removing the protecting group $P_1$ to produce a compound of formula B3:

B3 wherein
compound B3 contains at least two isotopic labels, and then intramolecularly dehydrating B3 (e.g. refluxing benzene with a Dean-Stark trap) to form a compound of formula B4:

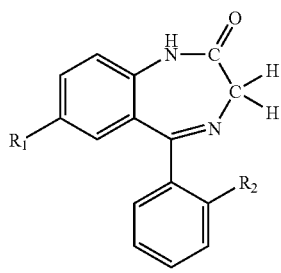

B4 wherein
compound B4 contains at least two isotopic labels.

(b) For compounds of Formula I, wherein there is a C—N single bond between nitrogen 1 and carbon 2, $X_1$ is oxygen and there is a C=O double bond between $X_1$ and carbon 2, and $R_3$ is hydrogen, $R_4$ is no substituent, and $X_2$ is methyl (—$CH_3$), —$CH_2CH_2N(CH_2CH_3)_2$, trifluoroethyl (—$CH_2CF_3$), or methylenecyclopropyl

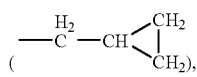

comprising treating an isotopically labeled compound B4 with a strong base (e.g. sodium hydride), and then treating the compound with an alkyl halide such as $CH_3I$, I—$CH_2CH_2N(CH_2CH_3)_2$, I—$CH_2CF_3$, or

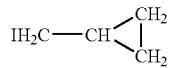

to produce a compound of formula B5:

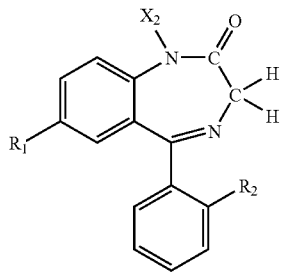

B5 wherein
compound B5 contains at least two isotopic labels.

(c) For compounds of Formula I, wherein there is a C—N single bond between nitrogen 1 and carbon 2, $X_2$ is hydrogen or methyl, $X_1$ is oxygen and there is a C—O double bond between $X_1$ and carbon 2, and $R_3$ is hydroxy, and $R_4$ is no substituent, comprising reacting a compound of Formula B5:

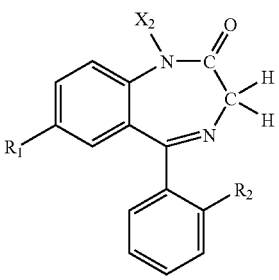

B5 wherein
compound B5 contains at least two isotopic labels with an electron poor peroxyacid,
then treating the resulting product with a compound of formula B6,

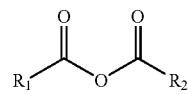

B6 wherein
$R_1$ and $R_2$ are independently selected from $C_1$-$C_6$ alkyl, and then saponifying (i.e., hydrolysis) of the ester intermediate.

(d) For compounds of Formula I, wherein there is a C—N single bond between nitrogen 1 and carbon 2, $X_1$ and $X_2$ together represent the bridge

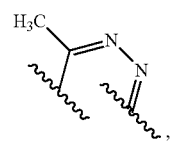

and $R_3$ is hydrogen and $R_4$ is no substituent, comprising treating a compound of Formula B7,

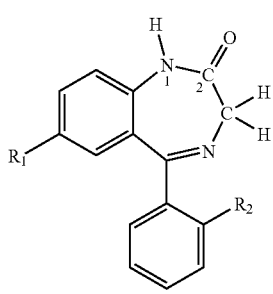

B7 wherein
compound B7 contains at least two isotopic labels, with a base, then reacting the compound with diethylchloropliosphate and then reacting the a compound with a compound of formula B8

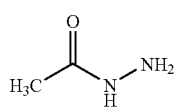

See Walser et. al *J. Med. Chem.* (1991) 34, 1209-1221 for methods of making triazole rings.

e) For compounds of Formula I, wherein there is a C—N double bond between nitrogen 1 and carbon 2, $X_2$ is no substituent, $X_1$ is methylamino and there is a C—N single bond between $X_1$ and carbon 2, $R_3$ is hydrogen, and $R_4$ is oxygen, a compound of Formula B9

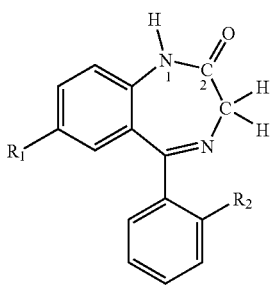

is treated with mCPBA to form a compound of formula B10

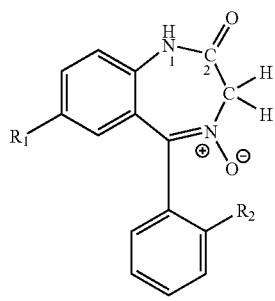

which is reacted with methylamine using titanium tetrachloride as a catalyst.

Preparation Methods for Labeled Benzodiazepines:

The compounds of Formula I can be prepared by the methods disclosed above using standard protocols known in the art of organic chemistry.

a) Respecting the compounds of Formula I wherein synthesis occurs via the compounds of Formula B3, reaction can occur in the presence of base and under the appropriate conditions for dehydration and imine condensation. Appropriate bases are, for example, pyridine, $NEt_3$, and Hunig's base and the reaction may be carried out in the presence of $Mg_2SO_4$, molecular sieves, or under Dean-Stark conditions for removal of water from the system. The condensation to form the diazepine ring structure can take place in neat base, or in the presence of a solvent such as toluene and is normally reacted under refluxing conditions. The reaction is stirred in air or under a nitrogen atmosphere until the water has been substantially removed from the system. Upon completion, the solvents can be removed iii vacuo and the crude product purified by recrystallization or by chromatography (e.g., silica gel or preparative HPLC). Optionally, the base can be removed by extraction with aqueous acid (e.g., ammonium chloride).

b) Respecting the compounds of Formula I wherein synthesis occurs between the compounds of Formula B5 and B6, reaction can occur in a suitable organic solvent (e.g.: $CH_2Cl_2$, $CHCl_3$, dimethylformamide etc.) or by the addition of a compound of Formula B5 to the neat anhydride. Generally, the reaction is heated to an appropriate temperature (e.g., 50-80° C.) until substantial conversion has been reached. Solvent and excess anhydride can then be removed in vacuo or the reaction system can be extracted with aqueous acid to remove the anhydride. The crude product purified by recrystallization (e.g., in ethanol) or by chromatography.

c) Respecting the compounds of Formula I wherein synthesis occurs between the compounds of Formula B7 and B8, reaction can occur by treating B7 (0.04 mol) in 350 mL of THF with potassium tert-butoxide (0.044 mol) and stirring under N2 for 30 min at −10 to −5 degrees celsius. Diethyl chlorophosphate (6.6 mL) is then added and the mixture is stirred at this temperature for another 30 min. Following the addition of acetic hydrazide (3.4 g), stirring without cooling is continued for 1 h and 1-butanol (150 mL) is added. The THF and part of the 1-butanol is distilled out of the reaction mixture over a period of 45 min. The residue is partitioned between toluene and water. The organic phase is washed with brine, dried, and evaporated.

d) Respecting the compounds of Formula I wherein synthesis occurs from a compound of Formula B10, reaction can occur by treating BIO with methylamine in tetrahydrofuran at ice-bath temperature with a tetrahydrofuran-titanium tetrachloride complex. For reference see: Fryer and co-workers, *J. Org. Chem.* (1969) 34, 1143-1145.

e) The compounds of Formula B5 can be prepared by a reaction of the compounds of Formula B11 wherein $R_5$ and X2 are selected from hydrogen or methyl,

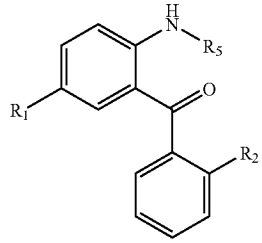

wherein
  the compound B1 can contain from zero to at least one isotopic labels;
with an isotopically labeled compound B2

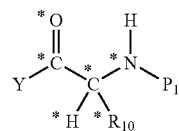

wherein
  at least one atom labeled with "*" is a stable isotope such as $^{13}C$ for C, $^{15}N$ for N, $^{18}O$ for O and $^2H$ for H; and
  $P_1$ is preferably tert-butoxycarbonyl (Boc) or benzyloxy carbonyl (Cbz).

The coupling of B1 and B2 can be carried out with the carboxylic acid functionality in place or with suitably activated derivatives of carboxylic acid, followed where necessary by subsequent removal of the amino protecting group. Suitably activated derivatives of the carboxylic acid include the corresponding acid halide (preferably the acid chloride), mixed anhydride or an activated ester (e.g., a thiol ester). The reaction is preferably carried out in a suitable aprotic solvent such as a halohydrocarbon (e.g. dichloromethane) or N,N-dimethylformamide and optionally in the presence of a tertiary base such as dimethylaminopyridine (DMAP) or triethylamine, or in the presence of inorganic base (e.g. sodium hydroxide) and at a temperature within the range of 0 to 120° C. The compounds of formulae B1 and B2 may also be reacted directly in the presence of a carbodiimide such as dicyclohexylcarbodiimide (DCC) or EDC. The deprotection of the amino protecting group, if appropriate, is carried out using techniques known in the art, for example; the Cbz group can be removed with hydrogenation in the presence of a palladium catalyst on carbon, or in the presence of an aqueous or organic acid.

f) The compounds of formula B6 are either commercially available, or can prepared by condensation of the appropriate carboxylic acids under dehydrating conditions.

g) The compounds of Formula B7 are prepared from the compounds of Formula B3 under the conditions set forth for the synthesis of the Formula I compounds wherein the Formula B3 compounds are employed as an intermediate.

h) Besides the above-mentioned reactions, the compounds of Formula I may be prepared by transforming other compounds of Formula I and it is to be understood that the present invention also comprises such compounds and processes. An example is set forth in above preparation method (i). An additional example could be the conversion of a Formula I compound wherein $X_2$ is hydrogen to a formula I compounds wherein $X_2$ is methyl. The reaction can be carried out in the presence of a base appropriate for nitrogen deprotonation (e.g., NaH, LDA, $K_2CO_3$, NaOtBu) and subsequent quenching of the nitrogen anion with a methyl electrophile (preferably MeI).

Synthesis of Labeled Amphetamines

Compounds of Formula II and pharmaceutically acceptable derivatives thereof may be prepared by the general methods outlined hereinafter, said methods constituting a further aspect of the invention. In the following description, the group $R_5$ has the meaning defined for the compounds of Formula II unless otherwise stated.

A further object of the present invention relates to the preparation of compounds of Formula II according to processes comprising:

(a) for compounds of Formula II, wherein $R_5$ has the meaning of hydrogen or methyl, reducing a compound of Formula A1

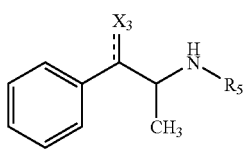

A1 wherein
compound A1 contains at least two isotopic labels; and $X_3$ is hydroxy or oxo.

(b) Additionally, for compounds of Formula II, wherein $R_5$ has the meaning of hydrogen, reducing a compound of Formula A2:

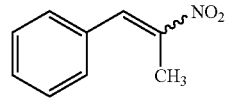

A2 wherein compound A2 contains at least two isotopic labels; and
the nitroalkene can be present in the E or Z form or as a mixture thereof.

(c) For compounds of Formula II, wherein $R_5$ has the meaning of hydrogen or methyl, reducing a compound of Formula A3

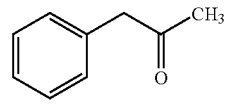

A3 wherein
compound A3 contains no or at least two isotopic labels;
in the presence of $NHR_6$, wherein $R_6$ is selected from hydrogen or methyl (d) For compounds of Formula II, wherein $R_1$ has the meaning of methyl, reducing a compound of formula A4

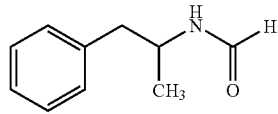

A4 wherein
compound A4 contains no or at least two isotopic labels.

(e) For compounds of Formula II, wherein $R_5$ has the meaning of hydrogen, hydrolysis of sulfinate A5

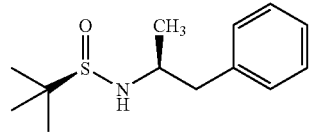

A5 wherein
compound A5 contains at least two isotopic labels.

Preparation Methods for Labeled Amphetamines:

(a) Respecting the compounds of Formula II wherein synthesis occurs via the compounds of Formula A1, reaction can occur in the presence of a reducing agent. Appropriate reducing agents are those capable of reducing a benzylic alcohol or ketone to a benzylic methylene (e.g., $LiAlH_4$). The reaction is carried out in an appropriate organic solvent, for example, THF, diethylether, or hexane, and at a temperature from 0° C. to 70° C. The reaction is stirred in air or under a nitrogen atmosphere until the benzylic oxygen has been substantially reduced, and upon completion excess reducing agent can be quenched by the addition of base (e.g., NaOH). Aluminium or boron salts can the be removed by filtration or aqueous extraction and the solvent can be removed in vacuo. The crude product can then purified by recrystallization or by distillation.

a) Respecting the compounds of Formula II wherein synthesis occurs via the compounds of Formula A2, reaction can occur in the presence of a reducing agent. Appropriate reducing agents are those capable of reducing a nitrostyrene to the corresponding phenethylamine (e.g., LiAlH$_4$). The reaction is carried out in an appropriate organic solvent, for example, THF, diethylether, or hexane, and at a temperature from 0° C. to 70° C. The reaction is stirred in air or under a nitrogen atmosphere until the benzylic oxygen has been substantially reduced, and upon completion excess reducing agent can be quenched by the addition of base (e.g., NaOH). Aluminium or boron salts can the be removed by filtration or aqueous extraction and the solvent can be removed in vacuo. The crude product can then be purified by distillation.

c) Respecting the compounds of Formula II wherein synthesis occurs via the compounds of Formula A3, reaction can occur in the presence of the appropriate amine base or salt, and with the appropriate reducing agent for a reductive amination (e.g., NaBH$_3$CN, NaBH(OAc)$_3$. For example, to a solution of a compound of formula A3 in THF, a solution of methyl amine in THF and solid NaBH(OAc)$_3$ are added. The reaction is stirred at an appropriate temperature (e.g., 25° C.) until the reduction is substantially complete and the reducing agent is then quenched with the addition of aqueous base. Reaction byproducts are then removed by extraction and the product can be purified by distillation.

d) Respecting the compounds of Formula II wherein synthesis occurs via the compounds of Formula A4, reaction can occur in the presence of a reducing agent. Appropriate reducing agents are those capable of reducing an N-formyl group to an N-methyl group (e.g., LiAlH$_4$). The reaction is carried out in an appropriate organic solvent, for example, THF, diethylether, or hexane, and at a temperature from 0° C. to 70° C. The reaction is stirred in air or under a nitrogen atmosphere until the benzylic oxygen has been substantially reduced, and upon completion excess reducing agent can be quenched by the addition of base (e.g., NaOH). Aluminum or boron salts can the be removed by filtration or aqueous extraction and the solvent can be removed in vacuo. The crude product can then be purified by distillation.

e) The compounds of Formula A1 can be prepared, for example, by a reacting phenyllithium (available commercially or prepared by the addition of an alkyllithium reagent to bromobenzene at low temperature (e.g., −78° C.) with a Weinreb amide of Formula A6.

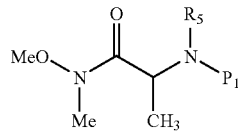

A6 wherein P$_1$ is hydrogen or a protecting group for an amine (e.g., Boc or Cbz).

The phenyllithium reagent is slowly added to the Weinreb amide at low temperature and the reaction is then allowed to warm to room temperature. Upon substantial conversion to product, the reaction is quenched by the addition of water or aqueous acid and the product purified by recrystallization of chromatography.

f) The compound of formula A2 can be prepared by the adding nitroethane to the appropriately isotopically labeled benzaldehyde (i.e., a Henry reaction). The reaction is carried out in an organic solvent, in acetic acid, or in an organic solvent/aqueous base biphasic mixture and in the presence of a base capable of deprotonating nitroethane (e.g., amine bases, NaOH). Additionally the reaction is performed under appropriate conditions such that the intermediate nitroaldol product is dehydrated to the nitrostyrene. The condensation can take place, for example, by heating the reaction mixture in acetic acid. The crude product can then be purified by recrystallization or chromatography.

g) Besides the above-mentioned reactions, the compounds of Formula II may be prepared by transforming other compounds of Formula II and it is to be understood that the present invention also comprises such compounds and processes. An example is set forth in above preparation method (d) wherein an isotopically labeled amphetamine can be converted to the corresponding methamphetamine be conversion to N-formyl amphetamine followed by reduction. N-formyl amphetamine can be prepared by the methods known in the art, for example, by reaction with formic acid under conditions appropriate for condensation (azetropic removal of water) or by reaction with formic acid in the presence of a peptide coupling reaction such as a carbodiimide (e.g., DCC or EDC). Additionally, the compound of Formula II wherein R$_5$ is methyl can be prepared from the compound of Formula II wherein R$_5$ is hydrogen by treatment of the latter with paraformaldehyde (or another formaldehyde equivalent know in the art) and reduction of the intermediate imine with a suitable reducing agent (e.g., LiAlH$_4$).

Synthesis of Labeled Methylphenidate

Figure 5:
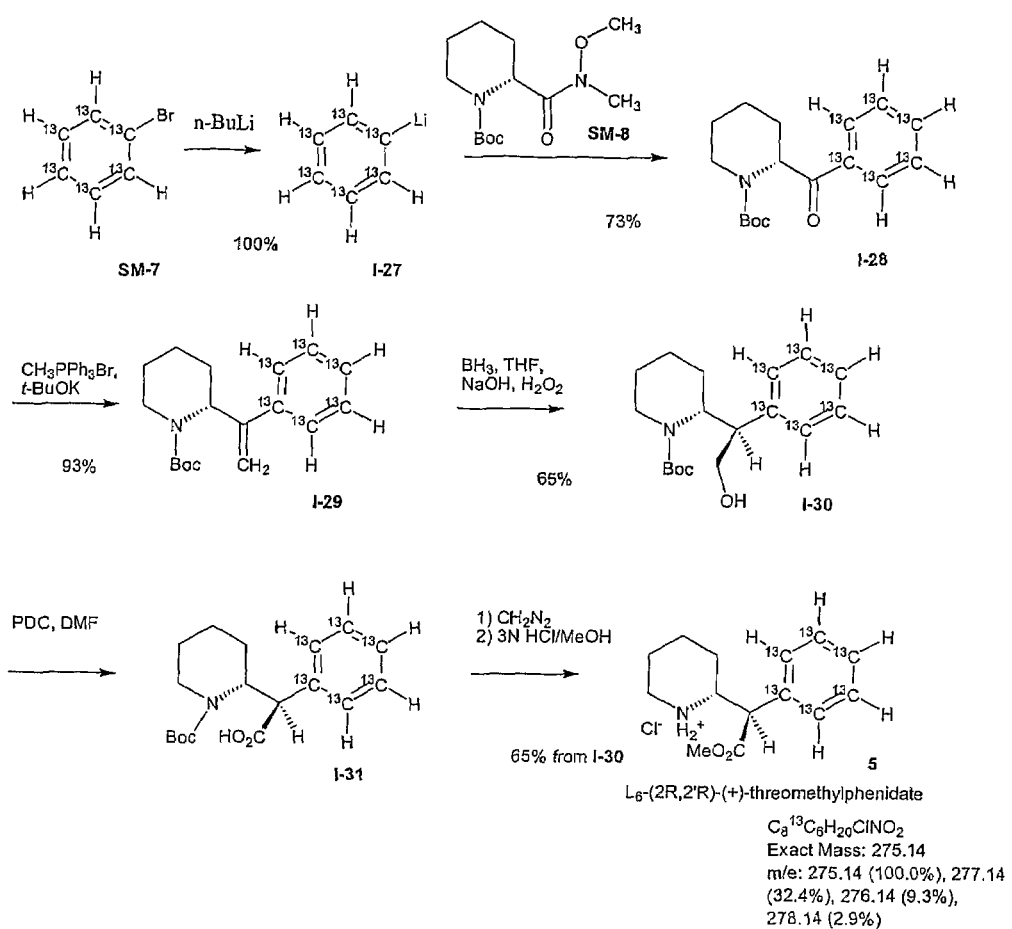
FIG. 5 shows the synthetic pathway for isotope labeled methylphenidate.

For a preparative method for the synthesis of labeled methylphenidate, refer to FIG. 5 and Example 5.

Synthesis of Labeled Fentanyl

For the synthesis of labeled fentanyl, coupling of a compound of Formula F1,

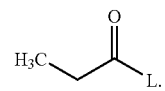

F1 wherein
    F1 contains one or more 1H, 13C, 18O labels; and
    L is hydroxy or an appropriate leaving group (e.g., chloride, thioester) with a compound of Formula F2,

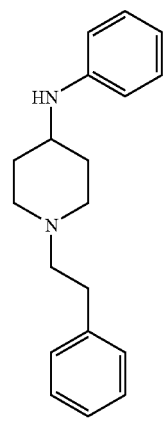

F2

When F1 is a labeled propionyl chloride, it can be synthesized from labeled propionic acid by treating the propionic acid with oxalyl chloride. Labeled propionic acids include propionic acid (1-13C, 99%), propionic acid (13C3, 99%), propionic acid (METHYL-D3, 98%), propionic acid (D5, 98%), propionic acid (2,2-D2, 98%), propionic acid (2,2-D2, 98%), and propionic acid (D6, 98%), which are commercially available from Cambridge Isotope Laboratories (Andover, Mass.).

For examples of fentanyl synthesis, see: Reference: Brine, G. A.; Boldt, K. G.; Huang, P.-T.; Sawyer, D. K.; Carroll, F. I.; JHTCAD; J. Heterocycl. Chem.; EN; 26; 1989; 677-686.

EXAMPLES

The present invention is also described by means of the following examples. However, the use of these or other examples anywhere in the specification is illustrative only and in no way limits the scope and meaning of the invention or of any exemplified term. Likewise, the invention is not limited to any particular preferred embodiments described herein. Indeed, many modifications and variations of the invention may be apparent to those skilled in the art upon reading this specification and can be made without departing from its spirit and scope. The invention is therefore to be limited only by the terms of the appended claims along with the full scope of equivalents to which the claims are entitled.

Example 1

Synthesis of $(1,2^{-13}C_2, 98\%)$ Lorazepam

The synthesis of double isotope labeled lorazepam was carried out using a modification of the protocol set forth in Koves, G. J. (*Journal of Radiolabeled Compounds and Radiopharmaceuticals* (1991) 29(1) 15-22) and described in detail in FIG. 1 and the following description.

Intermediate 1 (I-1): N-Cbz-$(1,2^{-13}C_2, 98\%)$-glycine

To a 500 mL three neck flask fitted with a reflux condenser, rubber septum, nitrogen adapter and magnetic stir bar will be added (U-$^{13}C_2$, 98%) glycine (SM-1) (8.9 g, 114.4 mmol). The solid will be suspended in 245 mL of $CH_2Cl_2$. Diisopropylethylamine (65.6 mL, 377.5 mmol) will be added with stirring. Chlorotrimethylsilane (65.6 mL, 514.8 mmol) will then be added slowly, and the solution refluxed for 1.5 hours. The flask will be transferred to an ice bath, and benzyl chloroformate (Cbz-Cl, 15.6 mL, 108.7 mmol) is added in one portion via syringe. The stirred solution will be allowed to warm to room temperature overnight. The reaction mixture will then be concentrated and added to 1 L of 2.5% aqueous $NaHCO_3$ and transferred to a separatory funnel. The solution will be washed with ether (3×200 mL). The ether washes will then be combined and back extracted with water (2×200 mL). The aqueous layers will be combined and acidified to pH 2 with 2M aqueous HCl. This solution will be extracted with EtOAc (4×250 mL). The EtOAc layers will be washed with brine (3×250 mL), dried over $Na_2SO_4$, and filtered. The solvent will be evaporated in vacuo, yielding the desired product I-1 (expected yield 21.7 g, 102.6 mmol, 95%)

Intermediate 2 (I-2): N-Cbz-$(1,2^{-13}C_2, 98\%)$-glycine acid chloride

To 100 mL of toluene will be added 5.6 g (27 mmol) triply labeled carbobenzyloxyglycine (I-1) to form a suspension. To this suspension will be added dimethylformamide (1 mL) and then oxalyl chloride (2.7 mL, 30 mmol) drop wise at room temperature. After ten minutes the solution should become clear. At this point the toluene, excess oxalyl chloride and HCl will be removed under reduced pressure. The residual oil will be dissolved in dry toluene and the toluene will be removed under reduced pressure yielding the desired product I-2 (expected yield 6.2 g, 27 mmol, quantitative). The acid chloride I-2 will be used without further purification.

Intermediate 3 (I-3): $(1,2^{-13}C_2, 98\%)$-{[4-Chloro-2-(2-chloro-benzoyl)-phenylcarbamoyl]-methyl}-carbamic acid benzyl ester To 8 mL of dry ether will be added 1.4 g (6.07 mmol) of the triply labeled Cbz-glycine acid chloride (I-2). To this solution will be added dropwise 1.65 g (6.2 mmol) of (2-amino-5-chlorophenyl)(2-chlorophenyl)methanone (SM-2) dissolved in 30 mL of dry ether over 40 min. A crystal slurry should form and it will be stirred for another two hours. The pH will be adjusted to 11 by slow addition of 5N NaOH and the solution will be stirred for another two hours. The ether layer will be separated and washed with water several times followed by several washes with 1M HCl. The organic extracts will be dried over anhydrous $Na_2SO_4$. The filtered solution will be evaporated in vacuo. The residue will be crystallized in 100 mL ethanol to produce I-3 (expected yield 2.4 g, 5.3 mmol, 85%).

Intermediate 4 (I-4): $(1,2^{-13}C_2, 98\%)$-2-Amino-N-[4-chloro-2-(2-chloro-benzoyl)-phenyl]-acetamide A solution of 1.5 g (3.26 mmol) of I-3 and 8 mL of 30% HBr in acetic acid will be stirred for 1 hour at room temperature. After 1 hour 100 mL of dry ether will be added and the mixture will be stirred for five minutes. The ether solution will be decanted and the precipitate will be washed with 50 mL of dry ether. The solid will be suspended in 25 mL of ether, chilled in an ice bath and 8 mL of 10% NaOH will be added. This mixture will be stirred and the ether will then be separated, washed with water and evaporated under reduced pressure to yield I-4 (expected yield 1.06 g, 3.26 mmol, quantitative yield). The product I-4 will be used without further purification.

Intermediate 5 (I-5): $(1,2^{-13}C_2, 98\%)$-7-Chloro-5-(2-chloro-phenyl)-1,3-dihydro-benzo[e][1,4]diazepin-2-one To 25 mL freshly distilled pyridine will be added 1.06 g (3.26 mmol)$_{I-4}$. The solution will be refluxed under nitrogen atmosphere for 16 hr. The pyridine will be evaporated under reduced pressure and the residue purified by preparative HPLC (mobile phase: $MeOH:H_2O$, 80:20, flow rate: 10 mL/min) fractions containing I-5 will be combined, evaporated and crystallized in ethanol (expected yield 1 g, 3.26 mmol, quantitative yield).

Intermediate 6 (I-6): $(1,2^{-13}C_2, 98\%)$-7-Chloro-5-(2-chloro-phenyl)-4-oxy-1,3-dihydro-benzo[e][1,4]diazepin-2-one A solution of 1 g (3.26 mmol) of I-5 in 50 mL of $CH_2Cl_2$ will be added dropwise to a stirred solution of 0.83 g (4.8 mmol) m-chloroperoxybenzoic acid (previously washed with a pH 7.4 buffer solution and dried in vacuo) in 10 mL of $CH_2Cl_2$ at 20 to 25° C. The solution will be stirred for 10 hours at room temperature and then another 0.83 g (4.8 mmol) m-chloroperoxybenzoic will be added. After another 10 hours of constant stirring the reaction mixture will be brought to pH 8.0 with 25% ammonium hydroxide and washed thoroughly with water. The solid white precipitate will be filtered and dried in vacuo. The combined solids will be crystallized from 7 mL of ethanol to produce the product I-6 (expected yield 0.8 g, 2.47 mmol, 75%).

Intermediate 7 (I-7): (1,2-$^{13}C_2$, 98%)-Acetic acid 7-chloro-5-(2-chloro-phenyl)-2-oxo-2,3-dihydro-1H-benzo[e][1,4]diazepin-3-yl ester A suspension of 1.0 g (3.1 mmol) of I-6 in 10 mL of acetic anhydride will be stirred and heated on a water bath for three hours at 60-70° C. Once the solution clears it will be evaporated in vacuo and the residue will be dissolved in 5 mL of ethanol and crystallized to produce the product 1-7 (expected yield 1.0 g, 2.75 mmol, 88%).

(1,2-$^{13}C_2$, 98%)-Lorazepam

One gram of I-7 (2.75 mmol) will be dissolved in 10 mL of methanol and then 6 mL of 4N NaOH will be added. After 30 min, a solid precipitate is expected that will dissolve on the addition of 50 mL water. The solution will be acidified with acetic acid and extracted with $CH_2Cl2$. After separation, the $CH_2Cl_2$ will be washed three times with 20 mL of water, dried on $Na_2SO_4$ and evaporated in vacuo. The solid will be purified on preparative HPLC (mobile phase: $MeOH:H_2O$, 30:70, flow rate: 10 mL/min). Fractions containing 1 will be combined, evaporated and crystallized in 2 mL ethanol to produce pure 1 (0.47 g, 1.46 mmol, 53%).

Example 2

Synthesis of (1,2-$^{13}C_2$-3-$^{15}N$, 98%) Lorazepam

Figure 2:
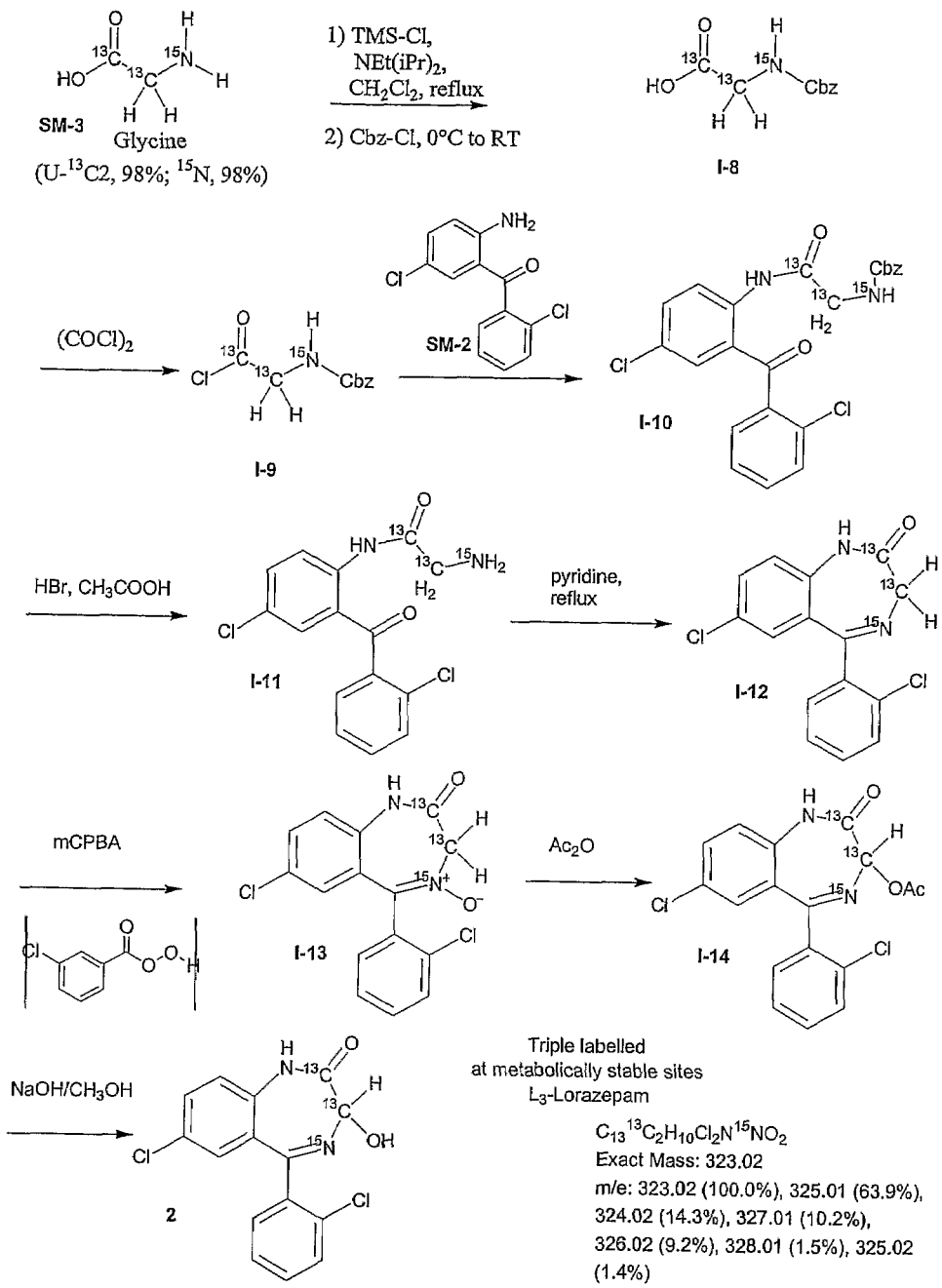
FIG. 2 shows the synthetic pathway for triple isotope labeled lorazepam.

The synthesis of triple isotope labeled lorazepam was carried out using a modification of the protocol set forth in Koves, G. J. (*Journal of Radiolabeled Compounds and Radiopharmaceuticals* (1991) 29(1) 15-22) and is described in FIG. 2. The synthesis is a modification of the protocol set forth in Example 1 with the only difference in the synthetic details being the use of (U-$3C_2$, 98%, $^{15}N$, 98%) glycine (SM-3) as the amino acid precursor.

Example 3

Synthesis of (1,2-$^{13}C_2$-3-$^{15}N$, 98%) Oxazepam

Figure 3:
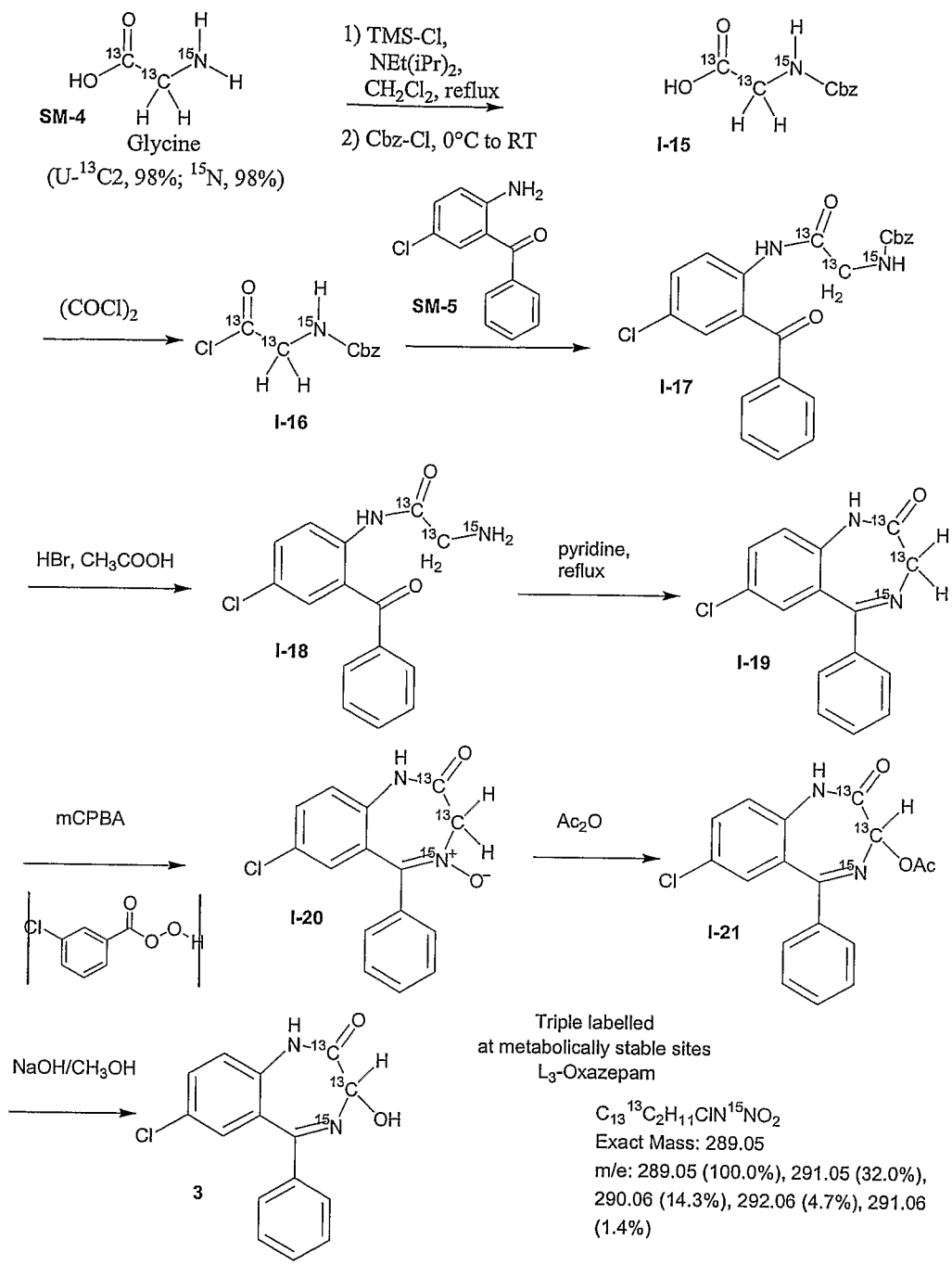
FIG. 3 shows the synthetic pathway for triple isotope labeled oxazepam.

The synthesis of triple isotope labeled oxazepam was carried out using a modification of the protocol set forth in Koves, G. J. (*Journal of Radiolabeled Compounds and Radiopharmaceuticals* (1991) 29(1) 15-22) and is described in FIG. 3. The synthesis is a modification of the protocol set forth in Example 1 with the only difference in the synthetic details being the use of (U-$^{13}C_2$, 98%, $^{15}N$, 98%) glycine (SM-3) as the amino acid precursor and (2-amino-5-chloro)-benzophenone as the benzophenone precursor (SM-5).

Example 4

Synthesis of (1,2-$^{13}C_2$-3-$^{15}N$, 98%) Clonazepam

Figure 4:
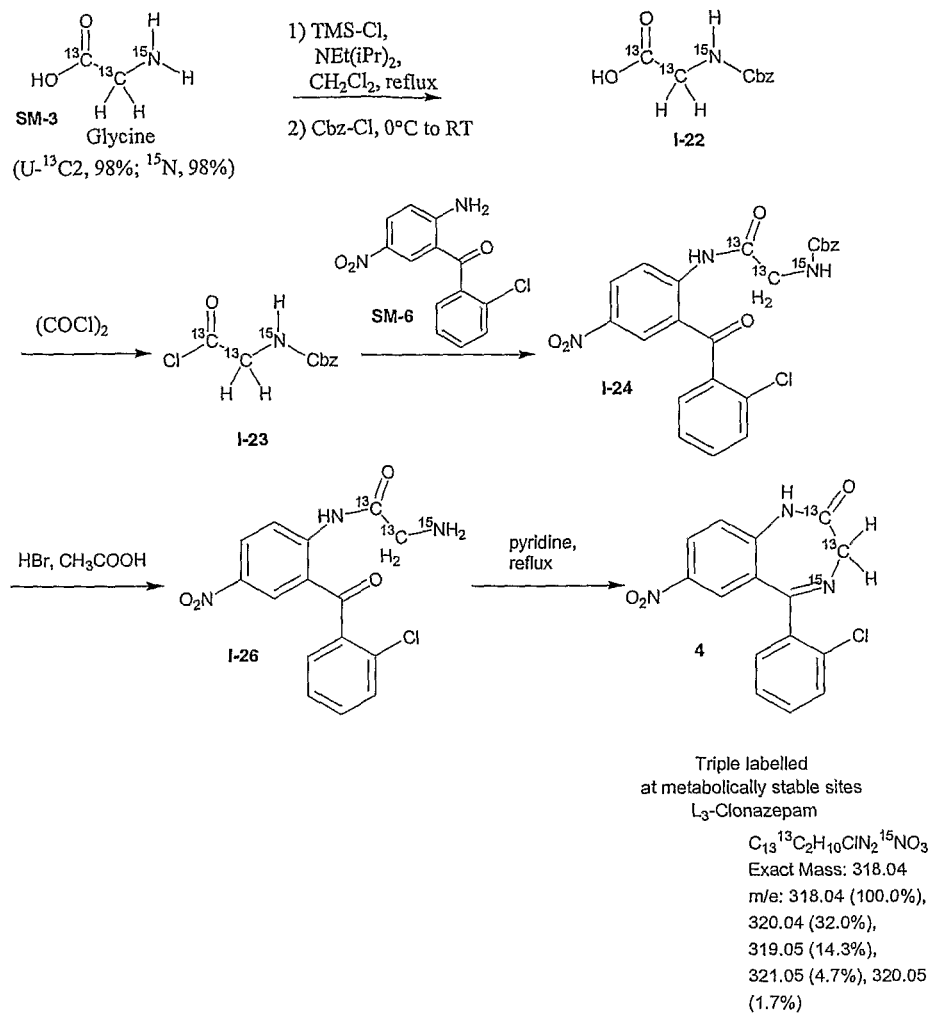
FIG. 4 shows the synthetic pathway for triple isotope labeled clonazepam.

The synthesis of triple isotope labeled clonazepam was carried out using a modification of the protocol set forth in Koves, G. J. (*Journal of Radiolabeled Compounds and Radiopharmaceuticals* (1991) 29(1) 15-22) and Sternbach, L. H. et al. (*Journal of Medicinal Chemistry*, (1963) 6, 261-265) and is described in FIG. 4. The synthesis is a modification of the protocol set forth in Example 1 with the only difference in the synthetic details being the use of (U-$^{13}C_2$, 98%, $^{15}N$, 98%) glycine (SM-3) as the amino acid precursor and (2-amino-5-chloro)-benzophenone as the benzophenone precursor (SM-6). Additionally, Clonazepam synthesis is complete upon cyclization to form the diazepine ring system (i.e., conversion of I-26 to 4).

Example 5

Synthesis of $^{13}C_6$-(2R,2'R)-(+)-Threomethylphenidate Hydrochloride

The synthesis of isotope labeled methylphenidate was carried out using a modification of the protocol set forth in Thai et al. (*J. Med. Chem.* (1998), 41, 591-601) and is described in FIG. 5 and the following written description.

Intermediate 27 (I-27)

Under a nitrogen atmosphere, a solution of $^{13}C_6$-bromobenzene (SM-7) (37.98 mmol) in THF (25 mL) is to be cooled to −78° C. To this mixture is added s-BuLi (32.1 mL, 41.78 mmol, 1.3 M in cyclohexane) over 20 min with the temperature maintained at less than −50° C. The reaction mixture is aged for 15 min at −78°. The solvent is removed under reduced pressure and the residue is then redissolved in 20 μL hexanes to produce a 2 M solution of I-27.

Intermediate 28 (I-28)

A solution of hydroxamate SM-8 (400 mg, 1.47 mmol) in $Et_2O$ (6.3 mL) is brought to −23° C. under an inert atmosphere, and a 2.0 M solution of $^{13}C_6$ phenyl lithium I-27 in hexanes (735 microliters, 1.47 mmol) is added dropwise via syringe over 15 min. Stirring is continued at −23° C. for 3 h, after which the reaction mixture is poured into an ice-chilled 1 M $KH_2PO_4$ solution (20 mL). The aqueous layer is extracted with EtOAc (4×15 mL), and the combined EtOAc layer is dried, filtered, and evaporated. Chromatography over silica gel eluting with 7.5-20% EtOAc in hexanes gives 200 mg of ketone I-28 (47% yield) as well as 143 mg of recovered starting material SM-8. Synthesis of SM-8 and the above conditions are described in: That and co-workers, *J. Med. Chem.* (1998) 41, 591-601.

Intermediate 29 (I-29)

To a suspension of methyltriphenylphosphonium bromide (230 mg, 0.644 mmol) in THF (1.0 mL) is added solid potassium tert-butoxide (72.2 mg, 0.644 mmol), and the resulting yellow suspension is allowed to stir for 10 min. A solution of I-28 (124 mg, 0.429 mmol) in THF (2.0 mL) is then added dropwise via syringe and the reaction allowed to proceed for 5 min. The reaction is quenched with water (1.0 mL) and suspended between EtOAc (15 mL) and water (15 mL). The aqueous layer is extracted with EtOAc (2×15 mL). The combined EtOAc layers are dried, filtered, and evaporated to an oil which is then filtered through a plug of silica gel eluting with 9% EtOAc in hexanes to give 115 mg (93%) of I-29 as a colorless oil. See That and co-workers, *J. Med. Chem.* (1998) 41, 591-601.

Intermediate 30 (I-30)

To a solution of I-29 (115 mg, 0.4 mmol) in THF (2.0 mL) is added 1.0 M $BH_3$.THF (800 microliters, 0.8 mmol) dropwise at room temperature via syringe over about 5 min. The reaction mixture is then stirred for 4 h after which water (1.0 mL), 3 N NaOH (1.0 mL), and 30% $H_2O_2$ (2.0 mL) are added consecutively. Stirring is continued overnight. The resulting mixture is suspended between EtOAc (20 mL) and water (15 mL), and the aqueous layer is extracted with EtOAc (3×10 mL). The combined EtOAc layers were dried, filtered, and evaporated to an oil which is purified by silica gen chromatography eluting with 16-20% EtOAc in hexanes. The less polar (1R,2R)-1-30 is obtained as a white solid (78 mg, 64% yield). See That and co-workers, *J. Med. Chem.* (1998) 41, 591-601.

Intermediate 31 (I-31)

Alcohol I-30 (228 mg, 0.748 mmol) is dissolved in DMF (3.0 mL), and PDC (984 mg, 2.62 mmol) is added. After 17 h of stirring, the reaction is quenched with water (40 mL) and the resulting mixture extracted with $Et_2O$ (6×20 mL). Combined Et2O layers are then extracted with 0.5 N NaOH (4×30 mL) and the alkaline solution brought to pH=~2.0 with 3 N HCl. A white precipitate is formed and is extracted into EtOAc (4×30 mL) which is dried, filtered, and evaporated under reduced pressure to give a crude colorless oil containing the carboxylic acid I-31 (194 mg). See That and co-workers, *J. Med. Chem.* (1998) 41, 591-601.

$^{13}C_6$-(2R,2'R)-(+)-threomethylphenidate 5

A portion (180 mg) of the crude oil I-31 is treated with excess diazomethane in ether (10 mL). The solution is evaporated to a light yellow oil which is stirred in 3 N methanolic HCl (10 mL) at room temperature overnight. Evaporation under reduced pressure provides a crude off-white solid which is recrystallized from $EtOH/Et_2O$ to give 125 mg of (2R,2'R)-5 as a white solid (67% yield from (1R,2R)-I-30).

Example 6

Synthesis of Deuterium Labeled Codeine

Figure 6:
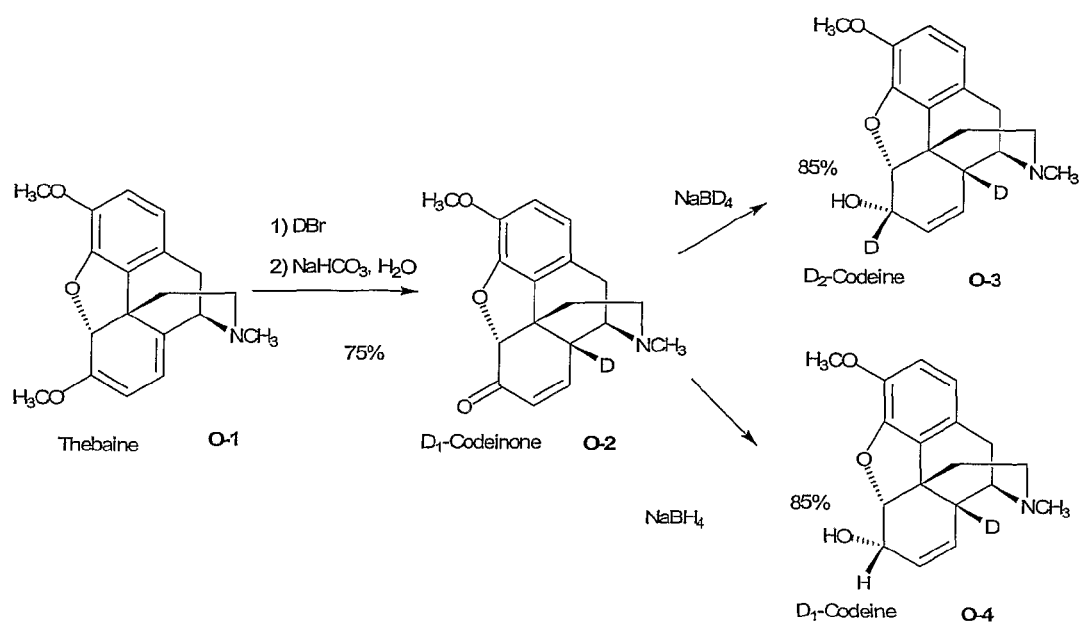
FIG. 6 shows the synthetic pathways for single and double isotope labeled codeine.

This example shows the synthesis of deuterium (D) labeled codeine from Thebaine, a natural opioid that is produced in high quantities by some varieties of *Papaver somniferum* (Blakemore P R, White J D, Chem. Comm. 2002: 1159-1168). See FIG. 6.

$D_1$-Codeinone O-2

A stirred solution of 100 g Thebain O-1 in $CH_2Cl_2$ (1 L) is cooled to below 3° C. in an ice-salt bath and then rapidly saturated with anhydrous DBr with continued cooling. The temperature is kept below 15° C. by controlling the rate of DBr addition. The DBr is added until the solution is saturated (~35 min). as indicated by a drop in temperature. The mixture is then cooled below 5° C. and poured into cold, stirred saturated $NaHCO_3$ solution (2 L). The neutral mixture is adjusted to pH 12 by the addition of 50% NaOH solution. The organic layer is separated and the aqueous phase washed twice with $CH_2Cl2$ (400 mL). The organic phases are combined, dried over anhydrous $Na_2SO_4$ and the solvent is remove in vacuo to leave a semicrystalline brown residue. The residue is triturated with MeOH (100 mL) and chilled. The crystals are collected and washed with three portions of cold MeOH (20 mL). These crystals are suspended in $H_2O$ and, with warming and stirring, the mixture is adjusted to pH 1-2 by the addition of concentrated HCl. The clear yellow solution is cooled in ice to 30° C., and 50% NaOH is added to give a thick suspension (pH approx. 14). The suspension is cooled below 15° C., and the crystals are collected, pressed dry, and then washed with cold water. The crystals should be dried overnight under high vacuum at 651C to give 64.5 g (67%) of O-2.

See Kotick M. P.; Leland, D. L, Polazzi, J. O.; Schut, R. N. *J. Med. Chem.* (1980) 23, 166-174.

$D_2$-Codeine (O-3)

To a solution of 194 mg of D1-codeinone O-2 in 10 ml methanol is added 0.5 g sodium borodeuteride ($NaBD_4$) which has been suspended in 12 ml methanol. The mixture is allowed to stand for 1.5 hours, concentrated to 10 ml in vacuo and diluted with 10 ml of 10% sodium hydroxide. The clear colorless solution is heated momentarily to boiling, diluted with water and extracted four times with chloroform. The washed, dried and filtered chloroform extract is then recrystallized from dilute methanol to give an expected yield of 173 mg D2-Codeine (O-3). See Gates, M. *J. Am. Chem. Soc.* (1953) 17, 4340-4341.

$D_1$-Codeine (O-4)

To a solution of 194 mg of D1-codeinone O-2 in 10 ml methanol is added 0.5 g sodium borohydride which has been suspended in 12 ml methanol. The mixture is allowed to stand for 1.5 hours, concentrated to 10 ml in vacuo and diluted with 10 ml of 10% sodium hydroxide. The clear colorless solution is heated momentarily to boiling, diluted with water and extracted four times with chloroform. The washed, dried and filtered chloroform extract is then recrystallized from dilute methanol to give an expected yield of 173 ing D1-Codeine (O-4).

See Gates, M. *J. Am. Chem. Soc.* (1953) 17, 4340-4341.

Example 7

Synthesis of Deuterium and $^{18}O$ Labeled Oxycodone

Figure 7:
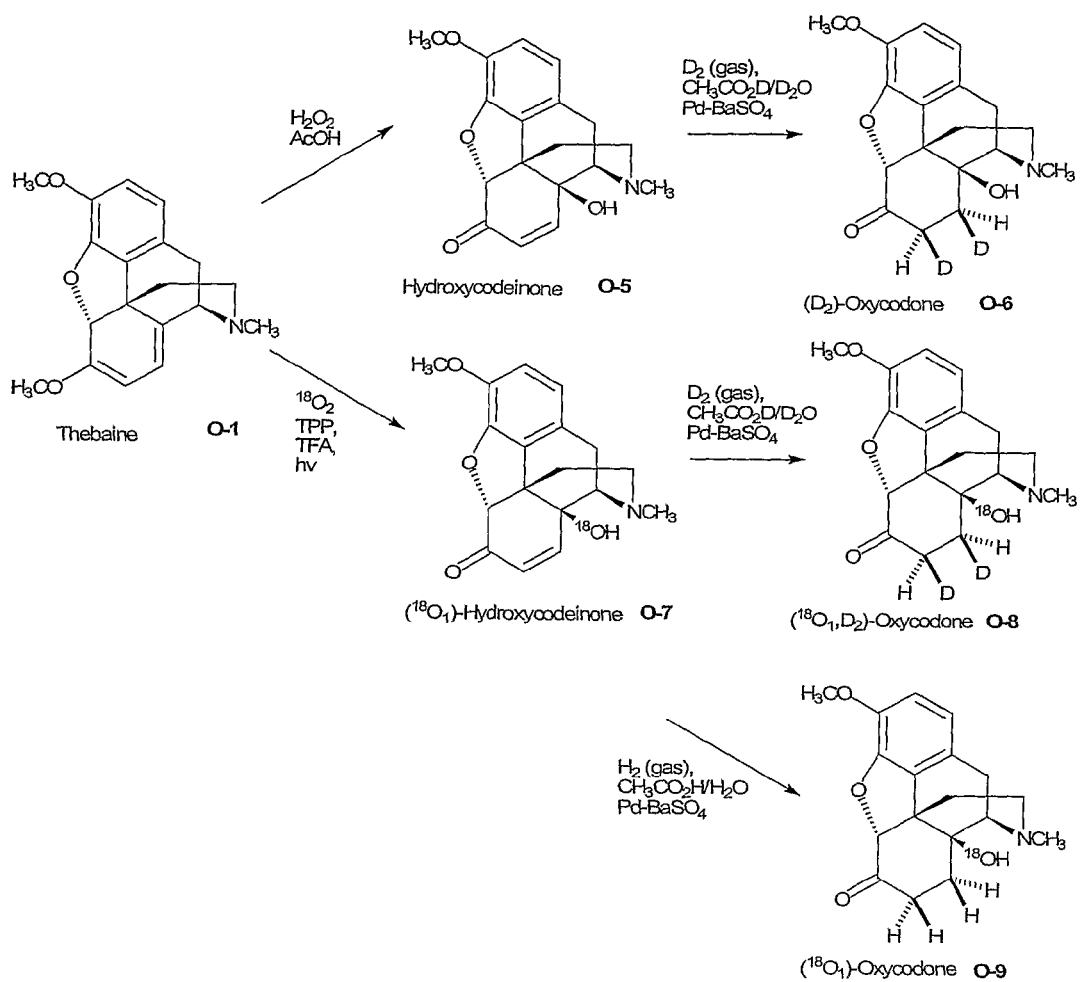
FIG. 7 shows the synthetic pathways for single, double and triple isotope labeled oxycodone.

This example describes the synthesis of deuterium and $^{18}O$ labeled oxycodone. See FIG. 7.

Hydroxycodeinone (O-5)

Hydrogen peroxide (30%, 1.3 mL, 13 mmol) is added to a solution of thebaine O-1 (3.11 g, 10 mmol) in a mixture of formic acid (88%, 1.3 mL) and $H_2SO_4$ (0.7%, 4.1 mL). The mixture is heated at 40° C. (bath temperature) for 6.5 h, cooled, diluted with water (10 mL), and made basic with concentrated $NH_4OH$. The precipitate is filtered, washed with $H_2O$ and dried ($MgSO_4$). The product is recrystallized from EtOH—$CHCl_3$ to yield O-5 (2.70 g, expected yield 86%). See Iijima, I.; Minamikawa, J.; Jacobson, A. E.; Brossi, A.; Rice, K. C.; *J. Med. Chem.* (1978) 21, 398.

(D2)-oxycodone (O-6)

To a solution of O-5 (2.00 g, 6.38 mmol) in deuteroacetic acid ($CH_3COOD$) (10% in $D_2O$, 40 mL) is added [Pd—$BaSO_4$ (5%, 1.00 g)]. The catalyst is then filtered and washed with $H_2O$ and the filtrate is made basic with concentrated $NH_4OH$. The solution is saturated with NaCl and extracted with $CHCl_3$. The extracts are washed with saturated NaCl solution and dried ($MgSO_4$), and the solvent is removed. The resulting crystalline solid is then washed with $Et_{20}$ and dried.

Expected yield of O-6 is 1.91 g (95%). See Iijima, I.; Minamikawa, J.; Jacobson, A. E.; Brossi, A.; Rice, K. C.; J. Med. Chem. (1978) 21, 398.

($^{18}O_1$)-hydroxycodeinone (O-7)

Thebaine O-1 (35 mg, 0.11 mmol) is combined with meso-tetraphenylporphyrin (5,10,15,20-tetraphenyl-21H,23H-porphrine; TPP) (5 mg, 0.03 mmol) in 50 mL of $CH_2Cl_2$. The solution is then acidified with trifluoroacetic acid to pH=4. $^{18}O$ oxygen ($^{18}O_2$) is circulated through the solution in a round-bottomed flask fitted with a cooling water-jacket [Currently >95% pure $^{18}O_2$ is available from Cambridge Isotope Laboratories]. The mixture is irradiated from a distance of 45 cm with an Osram Ultra-Vitalux sun lamp (300 W) for 55 min. The mixture is concentrated to 20 mL under reduced pressure and then 50 mL of ethyl ether is added. The resulting precipitate is decanted and washed with ethyl ether, affording an expected 25 mg of the trifluoroacetate salt of O-7 (61% yield). See Lopez, D.; Quinoa, E.; Riguera, R.; J. Org. Chem. (2000) 65(15) 4671-4678.

($D_2$,$^{18}O_1$)-oxycodone (O-8)

To a solution of O-7 (2.00 g, 6.38 mmol) in deuteroacetic acid ($CH_3COOD$) (10% in $D_2O$, 40 mL) is added [Pd—$BaSO_4$ (5%, 1.00 g)]. The solution is then placed under deuterium ($D_2$) gas atmosphere until the reaction is complete. The catalyst is then filtered and washed with $H_2O$ and the filtrate is made basic with concentrated $NH_4OH$. The solution is saturated with NaCl and extracted with $CHCl_3$. The extracts are washed with saturated NaCl solution and dried ($MgSO_4$), and the solvent is removed. The resulting crystalline solid then washed with $Et_2O$ and dried. Expected yield of O-8 is 1.91 g (95%). See Iijima, I.; Minamikawa, J.; Jacobson, A. E.; Brossi, A.; Rice, K. C.; J. Med. Chem. (1978) 21, 398.

($^{18}O_1$)-oxycodone (O-9)

To a solution of O-7 (2.00 g, 6.38 mmol) in acetic acid ($CH_3COOH$) (10% in $H_2O$, 40 mL) is added [Pd—$BaSO_4$ (5%, 1.00 g)]. The solution is then placed under hydrogen gas atmosphere ($H_2$) until the reaction is complete. The catalyst is then filtered and washed with $H_2O$ and the filtrate is made basic with concentrated $NH_4OH$. The solution is saturated with NaCl and extracted with $CHCl_3$. The extracts are washed with saturated NaCl solution and dried ($MgSO_4$), and the solvent is removed. The resulting crystalline solid O-9 is then washed with $Et_2O$ and dried. Expected yield of 0-9 is 1.91 g (95%). See Iijima, I.; Minamikawa, J.; Jacobson, A. E.; Brossi, A.; Rice, K. C.; J. Med. Chem. (1978) 21, 398.

Example 8

Synthesis of Deuterium Labeled Hydrocodone

Figure 8:
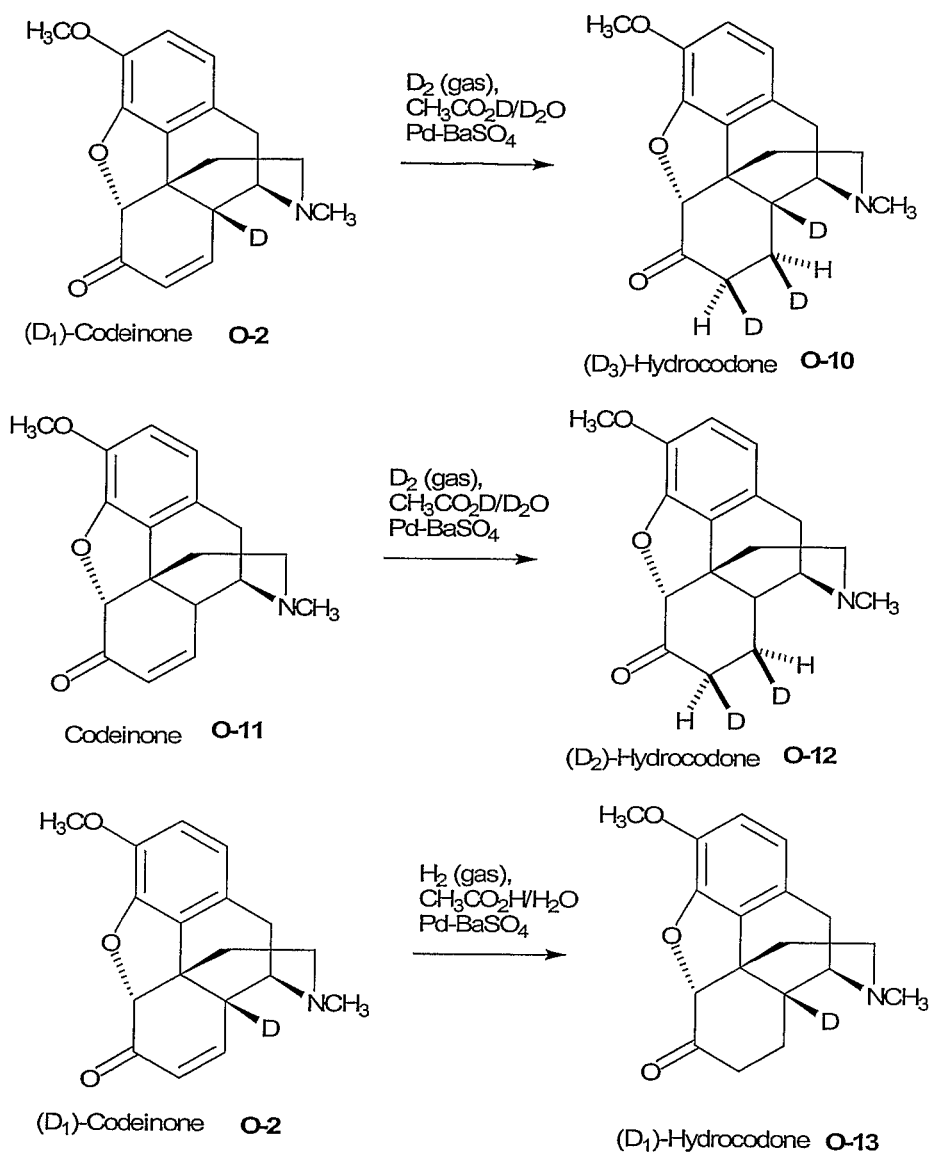
FIG. 8 shows the synthetic pathways for single, double and triple isotope labeled hydrocodone.

This example describes the synthesis of deuterium labeled hydrocodone. See FIG. 8.

(1D3)-hydrocodone (O-10)

To a solution of O-2 (2.00 g, 6.4 mmol) in deuteroacetic acid ($CH_3COOD$) (10% in $D_2O$, 40 mL) is added [Pd—$BaSO_4$ (5%, 1.00 g)]. The solution is then placed under deuterium ($D_2$) gas atmosphere until the reaction is complete. The catalyst is then filtered and washed with $H_2O$ and the filtrate is made basic with concentrated $NH_4OH$. The solution is saturated with NaCl and extracted with $CHCl_3$. The extracts are washed with saturated NaCl solution and dried ($MgSO_4$), and the solvent is removed. The resulting crystalline solid O-10 is then washed with $Et_2O$ and dried. Expected yield of O-10 is 1.9 g (95%). See Iijima, I.; Minamikawa, J.; Jacobson, A. E.; Brossi, A.; Rice, K. C.; J. Med. Chem. (1978) 21, 398.

(D2)-hydrocodone (O-12)

To a solution of Codeinone O-11 (2.00 g, 6.4 mmol) in deuteroacetic acid ($CH_3COOD$) (10% in $D_2O$, 40 mL) is added [Pd—$BaSO_4$ (5%, 1.00 g)]. The solution is then placed under deuterium ($D_2$) gas atmosphere until the reaction is complete. The catalyst is then filtered and washed with $H_2O$ and the filtrate is made basic with concentrated $NH_4OH$. The solution is saturated with NaCl and extracted with $CHCl_3$. The extracts are washed with saturated NaCl solution and dried ($MgSO_4$), and the solvent is removed. The resulting crystalline solid O-12 is then washed with Et2O and dried. Expected yield of O-12 is 1.9 g (95%). See Iijima, I.; Minamikawa, J.; Jacobson, A. E.; Brossi, A.; Rice, K. C.; J. Med. Chem. (1978) 21, 398.

($D_1$)-hydrocodone (O-13)

To a solution of ($D_1$)-Codeinone O-2 (2.00 g, 6.4 mmol) in acetic acid ($CH_3COOH$) (10% in $H_2O$, 40 mL) is added [Pd—$BaSO_4$ (5%, 1.00 g)]. The solution is then placed under hydrogen ($H_2$) gas atmosphere until the reaction is complete. The catalyst is then filtered and washed with $H_2O$ and the filtrate is made basic with concentrated $NH_4OH$. The solution is saturated with NaCl and extracted with $CHCl_3$. The extracts are washed with saturated NaCl solution and dried ($MgSO_4$), and the solvent is removed. The resulting crystalline solid O-13 is then washed with Et2O and dried. Expected yield of O-13 is 1.9 g (95%). See Ijima, I.; Minamikawa, J.; Jacobson, A. E.; Brossi, A.; Rice, K. C.; J. Med. Chem. (1978) 21, 398.

Example 9

Synthesis of $^{13}C$, $^{15}N$ Labeled Dextroamphetamine

Figure 9:
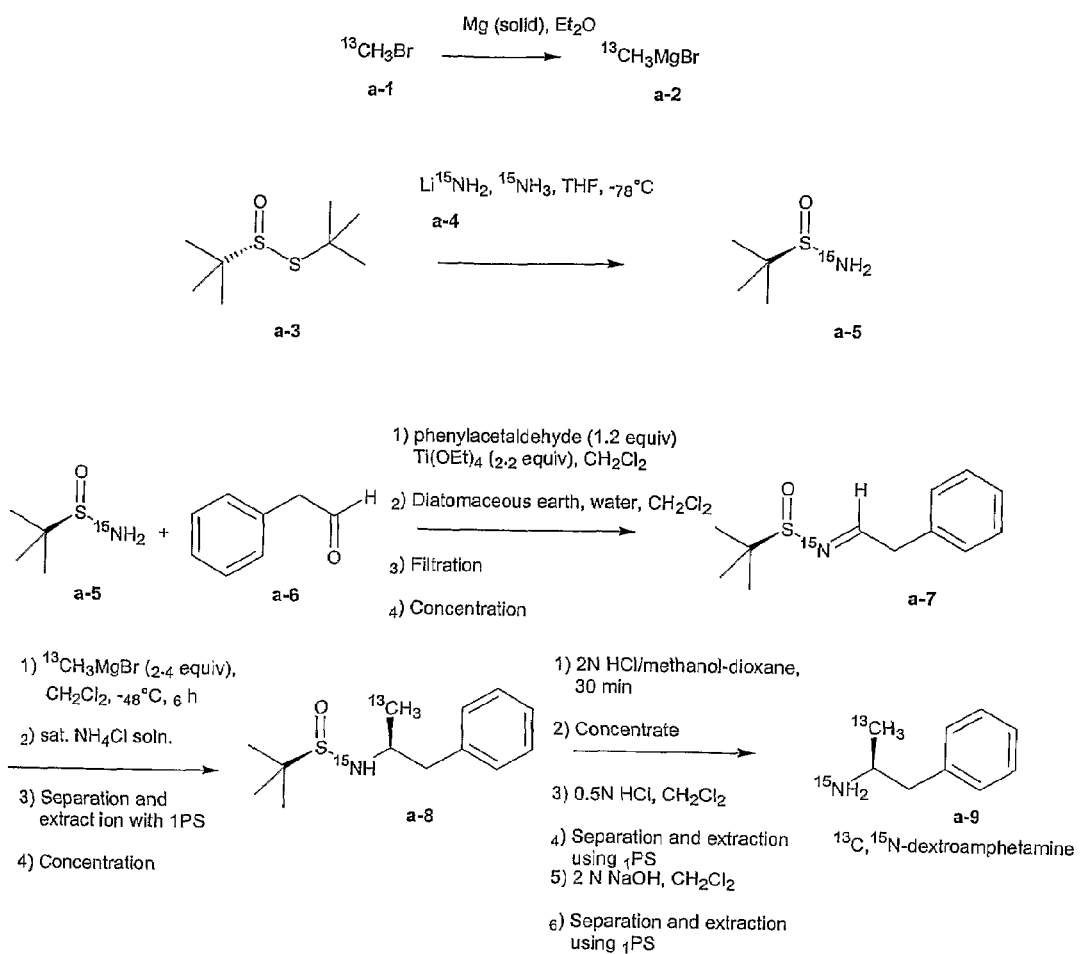
FIG. 9 shows the synthetic pathway for double labeled dextroamphetamine

This example describes the synthesis of $^{13}C$, $^{15}N$ labeled dextroamphetamine. See FIG. 9.

Intermediate a-2 ($^{13}C$ Methyl magnesium bromide)

$^{13}CH_3Br$ (a-1, 1.1 g, 11.7 mmol) is to be condensed into a 25 mL vacuum-line bulb. A dry ice/acetone condenser and a 100 mL Schlenk flask containing Reade high-purity magnesium turnings (218 mg, 8.97 mmol) are connected directly to a high-vacuum line through the side arm near the base of the condenser. The apparatus is then evacuated and diethyl ether (~25 mL) is transferred into the reaction flask and freeze-pump-thaw degassed. Before the final thawing the condenser is charged with dry ice/acetone and an aliquot of $^{13}CH_3Br$ is condensed into the reaction flask. The reaction mixture is allowed to warm slowly to room temperature; stirring is to be started after bubbling shows that the reaction has been initiated. The rest of the $^{13}CH_3Br$ is added in aliquots (using a mercury manometer to control the addition) at a rate that maintains gental reflux of the solution without external heating. After the addition is complete, the reaction is stirred until all of the magnesium is consumed (~1 h). The diethyl ether and excess $^{13}CH_3Br$ is removed under reduced pressure to yield a white crystalline product a-2, which is dried under vacuum for 1 h. The product is extracted with diethyl ether (35 mL) and filtered through a glass frit to give a clear, colorless solution (~0.36 M), which is used without further purification. See Bullock R. M. and co-workers, J. Am. Chem. Soc. (1989), 111, 3897-3908.

Intermediate a-5 ($^{15}$N—R-tert-butanesulfinamide)

A 5 L three-necked round bottomed flask equipped with a mechanical stirrer, an ammonia condenser, and a nitrogen inlet is charged with 2 L of liquid $^{15}$N-ammonia. A few crystals of Fe(NO$_3$)$_3$ are added and lithium wire (13.3 g, 1.92 mol) is added in ca. 500 mg portions. A −78 C bath is periodically raised to the bottom of the flask to abate any refluxing caused by the formation of Li$^{15}$NH$_2$. As lithium is added, the mixture will become blue, but fade to reveal a gray suspension. When all the lithium wire is added and the mixture has become gray, the flask is submerged into the −78 C bath. After 30 min a solution of thiosulfinate a-3 (92.9 g, 0.479 mol) in 500 mL of THF is slowly added over the course of an hour. Once the addition is complete the mixture is stirred an additional 15 min before 128 g (2.40 mol) of NH4Cl is added slowly and carefully. The cold bath is removed and stirring continued until the mixture reaches ambient temperature. The remaining volatile material is removed under aspirator pressure. To the remaining residue is added 250 mL of water with swirling to dissolve all the salts. The resulting mixture is extracted with 1.5 L of EtOAc (3×) and the organic layers washed once each with the same 150 mL of brine before they are combined and dried (Na2SO4). The solid remaining after removal of solvent is recrystallized once from hexanes to provide an expected yield of 45.6 g (79%) of enantiomerically pure $^{15}$N—R-tert-butanesulfinamide a-5. The synthesis of thiosulfinate a-3 and reaction with lithium amide is described in Liu, G. Cogan, D. A., Ellman, J. A. *J. Am. Chem. Soc.* (1997), 119, 9913-9914.

Intermediate a-7 ($^{15}$N-2-Methyl-propane-2-sulfinic acid [2-phenyl-eth-(E)-ylidene]-amide)

To a solution of $^{15}$N-tert-butanesulfinamide a-5 (0.12 g, 1.0 mmol) and phenyl-acetaldehyde a-6 (1.2 mmol) in CH$_2$Cl$_2$ (2.5 mL) is added titanium tetraethoxide (purity: 85-95%, 0.46 mL, 2 mmol) under a nitrogen atmosphere. The mixture is stirred at room temperature for 15 h. Diatomaceous earth (8 mL) is placed in a polypropylene SPE cartridge (12 mL, with 70 micrometer PE frit) equipped with a PTFE stopcock and then is soaked with water (2.5 mL). The reaction mixture is then to be transferred to the SPE cartridge while rinsing with 5 mL of CH$_2$Cl$_2$, and the cartridge is plugged with a glass stopper coated with PTFE seal tape. The cartridge is shaken vigorously for 30 s so that the diatomaceous earth flows freely in the cartridge. The mixture is shaken for 30 min with a wrist action shaker. During the mixing, the cartridge is shaken vigorously with hands at intervals to ensure effective mixing. The solid phase is filtered and washed with CH$_2$Cl$_2$ until no product can be found in the elution. The filtrate is evaporated and filtered through a 0.5-cm plug of silica gel (Merck 60 230-400 mesh) in a glass pipet. The silica gel is washed with a small amount of a 9:1 CH$_2$Cl$_2$/Et$_2$O mixture. The product imine a-7 (1.0 mmol) contaminated with excess aldehyde will be obtained by evaporation of the solvent from the filtrate. See Mukade, T. Dragoli, D. R. Ellman, J. A., *J. Comb. Chem.* (2003), 5, 590-596.

Intermediate a-8 ($^{13}$C-$^{15}$N-2-Methyl-propane-2-sulfinic acid ((S)-1-methyl-2-phenyl-ethyl)-amide)

The mixture containing 1 mmol of imine a-7 is dissolved in CH$_2$C12 (5 mL) and cooled to −48 C. To this cooled mixture, $^{13}$CH$_3$MgBr a-2 in diethyl ether (3.0 M, 0.800 mL, 2.40 mmol) is added slowly dropwise. The reaction mixture is stirred at −48 C for 6 h and then is allowed to gradually warm to room temperature. After stirring overnight, the reaction is quenched by the addition of saturated aqueous ammonium chloride solution (2 mL). After stirring vigorously for 10 min, the mixture is transferred to a 1PS filter cartridge equipped with a PTFE stopcock, and the organic phase is isolated. The aqueous phase is rinsed with dichloromethane (3×2 mL) and evaporated to afford the desired crude sulfonamide product a-8 (expected yield 77% with 91% ee). The product a-8 is used without further purification. See Mukade, T. Dragoli, D. R. Ellman, J. A., J. Comb. Chem. (2003), 5, 590-596.

Intermediate a-9 ($^{13}$C, $^{15}$N-dextroamphetamine)

The product a-8 (0.77 mmol) is dissolved in methanol (2 mL). To this mixture is added 4 N hydrogen chloride in 1,4-dioxane (2 mL). The mixture is stirred for 30 min and then concentrated to dryness. The obtained mixture is distributed in 0.5 N hydrochloric acid (2 mL) and dichloromethane (2 mL) and is then transferred to a 1PS filter cartridge (12 mL) equipped with a PTFE stopcock. The organic layer is removed, and the aqueous layer is washed with CH$_2$Cl$_2$ (3×2 mL). A 2 N sodium hydroxide solution (2 mL) is then added to the aqueous layer, and the resulting free amine was extracted with dichloromethane (3×2 mL). The solvent is then removed under reduced pressure to obtain a-9. See Mukade, T. Dragoli, D. R. Ellman, J. A., J. Comb. Chem. (2003), 5, 590-596.

Example 10

Synthesis of $^{13}$C, $^{15}$N Labeled Levamphetamine

Figure 10:
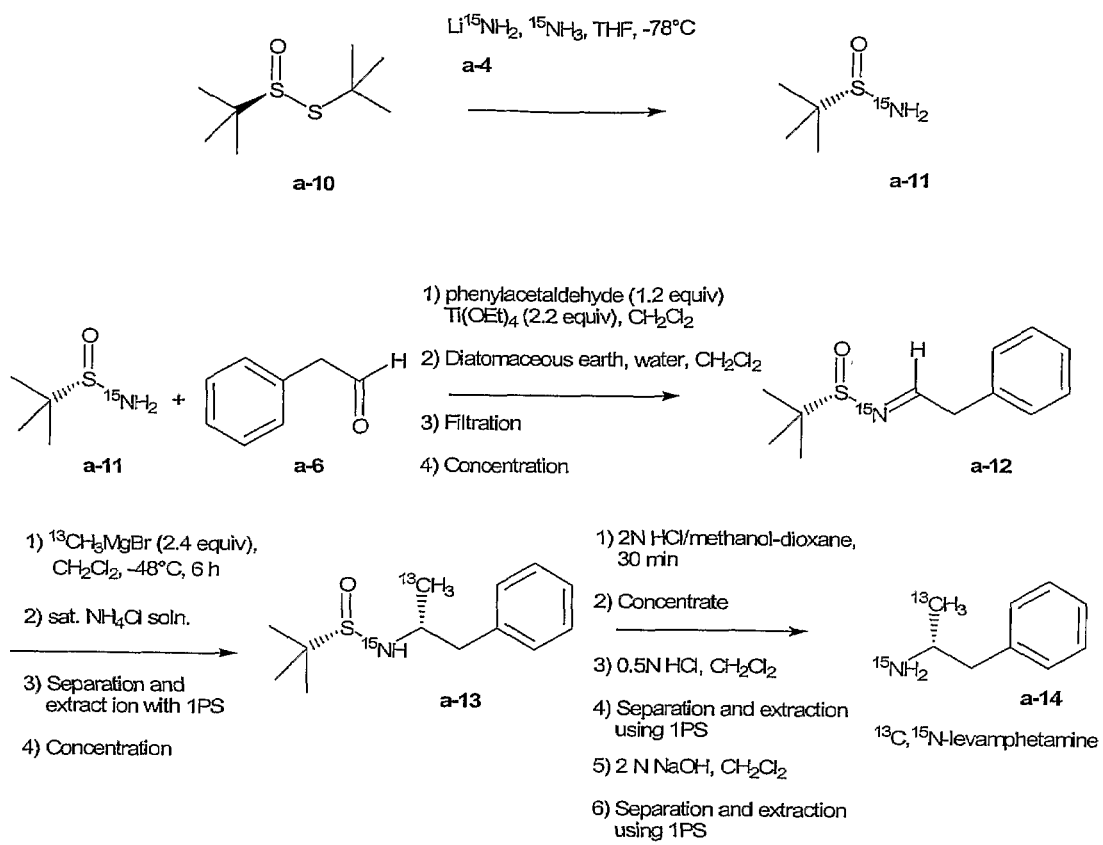
FIG. 10 shows the synthetic pathway double labeled levamphetamine

This example describes the synthesis of $^{13}$C, $^{15}$N labeled levamphetamine. See FIG. 10.

Intermediate a-11 ($^{15}$N—S-tert-butanesulfinamide)

A 5 L three-necked round bottomed flask equipped with a mechanical stirrer, an ammonia condenser, and a nitrogen inlet is charged with 2 L of liquid $^{15}$N-ammonia. A few crystals of Fe(NO$_3$)$_3$ are added and lithium wire (13.3 g, 1.92 mol) is added in ca. 500 mg portions. A −78 C bath is periodically raised to the bottom of the flask to abate any refluxing caused by the formation of Li$^{15}$NH$_2$. As lithium is added, the mixture will become blue, but fade to reveal a gray suspension. When all the lithium wire is added and the mixture has become gray, the flask is submerged into the −78 C bath. After 30 min a solution of thiosulfinate a-10 (92.9 g, 0.479 mol) in 500 mL of THF is slowly added over the course of an hour. Once the addition is complete the mixture is stirred an additional 15 min before 128 g (2.40 mol) of NH$_4$Cl is added slowly and carefully. The cold bath is removed and stirring continued until the mixture reaches ambient temperature. The remaining volatile material is removed under aspirator pressure. To the remaining residue is added 250 mL of water with swirling to dissolve all the salts. The resulting mixture is extracted with 1.5 L of EtOAc (3×) and the organic layers washed once each with the same 150 mL of brine before they are combined and dried (Na$_2$SO$_4$). The solid remaining after removal of solvent is recrystallized once from hexanes to provide an expected yield of 45.6 g (79%) of enantiomerically pure $^{15}$N—S-tert-butanesulfinamide a-11. The synthesis of thiosulfinate a-10 and reaction with lithium amide is described in Liu, G. Cogan, D. A., Ellman, J. A. *J. Am. Chem. Soc.* (1997), 119, 9913-9914.

Intermediate a-12 ($^{15}$N-2-Methyl-propane-2-sulfinic acid [2-phenyl-eth-(E)-ylidene]-amide)

To a solution of $^{15}$N-tert-butanesulfinamide a-11 (0.12 g, 1.0 mmol) and phenyl-acetaldehyde a-6 (1.2 mmol) in CH$_2$Cl$_2$ (2.5 mL) is added titanium tetraethoxide (purity: 85-95%, 0.46 mL, 2 mmol) under a nitrogen atmosphere. The mixture is stirred at room temperature for 15 h. Diatomaceous earth (8 mL) is placed in a polypropylene SPE cartridge (12 mL, with 70 micrometer PE frit) equipped with a PTFE stopcock and then is soaked with water (2.5 mL). The reaction mixture is then to be transferred to the SPE cartridge while rinsing with 5 mL of CH$_2$Cl$_2$, and the cartridge is plugged with a glass stopper coated with PTFE seal tape. The cartridge is shaken vigorously for 30 s so that the diatomaceous earth flows freely in the cartridge. The mixture is shaken for 30 min with a wrist action shaker. During the mixing, the cartridge is shaken vigorously with hands at intervals to ensure effective mixing. The solid phase is filtered and washed with CH$_2$Cl$_2$ until no product can be found in the elution. The filtrate is evaporated and filtered through a 0.5-cm plug of silica gel (Merck 60 230-400 mesh) in a glass pipet. The silica gel is washed with a small amount of a 9:1 CH$_2$C12/Et$_2$O mixture. The product imine a-12 (1.0 mmol) contaminated with excess aldehyde will be obtained by evaporation of the solvent from the filtrate. See Mukade, T. Dragoli, D. R. Ellman, J. A., *J. Comb. Chem.* (2003), 5, 590-596.

Intermediate a-13 ($^{13}$C—$^{15}$N-2-Methyl-propane-2-sulfinic acid ((S)-1-methyl-2-phenyl-ethyl)-amide)

The mixture containing 1 mmol of imine a-12 is dissolved in CH$_2$C12 (5 mL) and cooled to −48 C. To this cooled mixture, $^{13}$CH$_3$MgBr a-2 in diethyl ether (3.0 M, 0.800 mL, 2.40 mmol) is added slowly dropwise. The reaction mixture is stirred at −48 C for 6 h and then is allowed to gradually warm to room temperature. After stirring overnight, the reaction is quenched by the addition of saturated aqueous ammonium chloride solution (2 mL). After stirring vigorously for 10 min, the mixture is transferred to a 1PS filter cartridge equipped with a PTFE stopcock, and the organic phase is isolated. The aqueous phase is rinsed with dichloromethane (3×2 mL) and evaporated to afford the desired crude sulfonamide product a-13 (expected yield 77% with 91% ee). The product a-13 is used without further purification. See Mukade, T. Dragoli, D. R. Ellman, J. A., J. Comb. Chem. (2003), 5, 590-596.

a-14 ($^{13}$C, $^{15}$N-levamphetamine)

The product a-13 (0.77 mmol) is dissolved in methanol (2 mL). To this mixture is added 4 N hydrogen chloride in 1,4-dioxane (2 mL). The mixture is stirred for 30 min and then concentrated to dryness. The obtained mixture is distributed in 0.5 N hydrochloric acid (2 mL) and dichloromethane (2 mL) and is then transferred to a 1PS filter cartridge (12 mL) equipped with a PTFE stopcock. The organic layer is removed, and the aqueous layer is washed with CH$_2$Cl$_2$ (3×2 mL). A 2 N sodium hydroxide solution (2 mL) is then added to the aqueous layer, and the resulting free amine was extracted with dichloromethane (3×2 mL). The solvent is then removed under reduced pressure to obtain a-14. See Mukade, T. Dragoli, D. R. Ellman, J. A., J. Comb. Chem. (2003), 5, 590-596.

Examples 11-14

Synthesis of Mono-Labeled Amphetamines

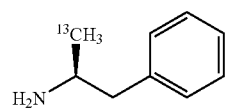
a-15

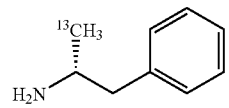
a-16

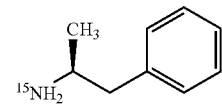
a-17

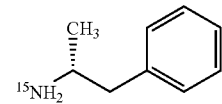
a-18

Example 11

($^{13}$C-dextroamphetamine) a-15

Prepare as described above for a-9 but use unlabeled NH$_3$ rather than $^{15}$NH$_3$.

Example 12

($^{13}$C-levamphetamine) a-16

Prepare as described above for a-14 but use unlabeled NH$_3$ rather than $^{15}$NH$_3$.

Example 13

($^{15}$N-dextroamphetamine) a-17

Prepare as described above for a-9 but use unlabeled CH$_3$Br rather than $^{13}$CH$_3$Br.

Example 14

($^{15}$N-levamphetamine) a-18

Prepare as described above for a-14 but use unlabeled CH$_3$Br rather than $^{13}$CH$_3$Br.

Example 15

13C,$^{15}$N-Benzedrine

Combine 1 equivalent a-9 and 1 equivalent a-14 with 1 equivalent H$_2$SO$_4$.

Example 16

$^{13}C$, $^{15}N$-Actemin

Combine 1 equivalent a-9 and 1 equivalent a-14 with 2 equivalents $H_3PO_4$.

Example 17

$^{13}C$, $^{15}N$-Dexamin (also called Dexedrine, Dextrostat)

Combine 1 equivalent a-9 and 1 equivalent of $H_2SO_4$.

Example 18

$^{13}C$, $^{15}N$-Tanphetamin (also called Synatan)

Combine 1 equivalent a-9 and 1 equivalent of Tannic acid.

Example 19

$^{13}C$-Benzedrine

Combine 1 equivalent a-15 and 1 equivalent a-16 with 1 equivalent $H_2SO_4$.

Example 20

$^{13}C$-Actemin

Combine 1 equivalent a-15 and 1 equivalent a-16 with 2 equivalents $H_3PO_4$.

Example 21

$^{13}C$-Dexamin (also called Dexedrine, Dextrostat)

Combine 1 equivalent a-15 and 1 equivalent of $H_2SO_4$.

Example 22

$^{13}C$-Tanphetamin (also called Synatan)

Combine 1 equivalent a-15 and 1 equivalent of Tannic acid.

Example 23

$^{15}N$-Benzedrine

Combine 1 equivalent a-17 and 1 equivalent a-18 with 1 equivalent $H_2SO_4$.

Example 24

$^{15}N$-Actemin

Combine 1 equivalent a-17 and 1 equivalent a-18 with 2 equivalents $H_3PO_4$.

Example 25

$^{15}N$-Dexamin (also called Dexedrine, Dextrostat)

Combine 1 equivalent a-17 and 1 equivalent of $H_2SO_4$.

Example 26

$^{15}N$-Tanphetamin (also called Synatan)

Combine 1 equivalent a-17 and 1 equivalent of Tannic acid.

Examples 27-29

Synthesis of Labeled Methamphetamine

Example 27

($^{13}C$, $^{15}N$-methamphetamine) a-19

Figure 11:
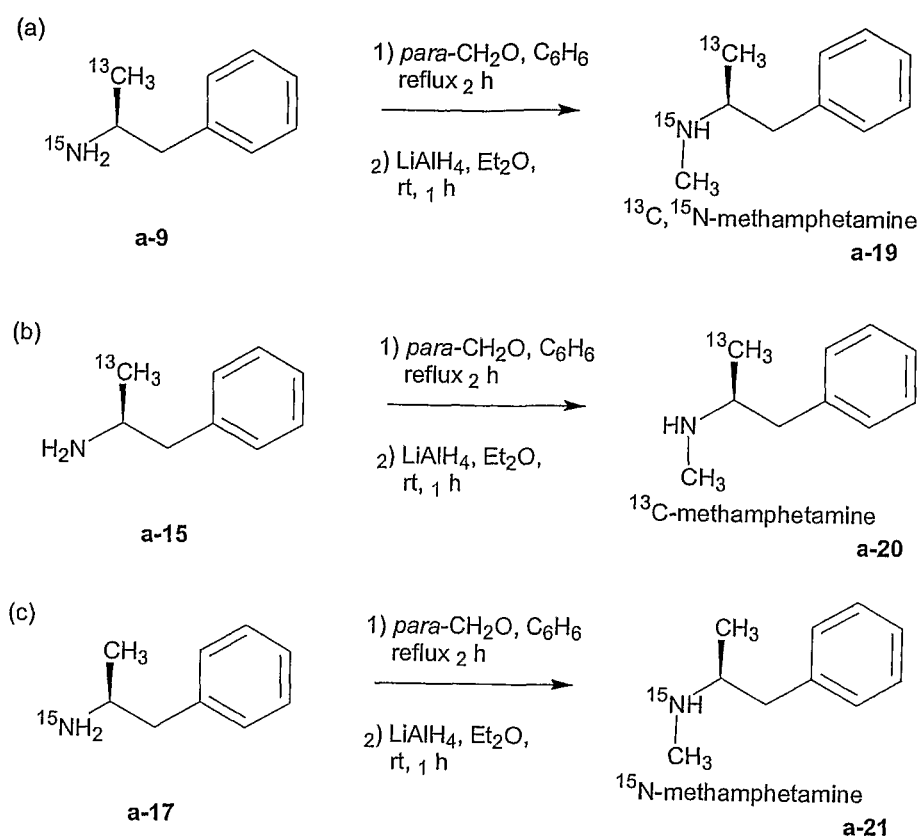
FIG. 11 shows the synthetic pathways for (a) $^{13}$C, $^{15}$N-methamphetamine, (b) $^{13}$C-methamphetamine, and (c) $^{15}$N-methamphetamine.

This example describes the synthesis of $^{13}C$, $^{15}N$-methamphetamine. See FIG. 11(*a*).

The amphetamine a-9 (10 mmol) is combined with 3.33 mmol para-formaldehyde in 50 mL dry benzene. The mixture is placed in a round bottom flask affixed with a Dean-Stark trap. The mixture is refluxed for two hours with continuous removal of water. The benzene is then removed using reduced pressure. To the residue is added 50 mL dry $Et_2O$ and an excess of $LiAlH_4$ is slowly added. The mixture is stirred for one hour at room temperature. The reaction is quenched slowly with water, and extracted with $CH_2Cl_2$. The organic layer is dried using anhydrous $MgSO_4$ and evaporated to produce labeled methamphetamine a-19. See Bartroli and co-workers, *J. Med. Chem.* (1998), 41, 1855-1868; Konosu and coworkers, *Chem. Pharm. Bull.* (1991), 39, 2581-2589.

Example 28

($^{13}C$-methamphetamine) a-20

This example describes the synthesis of $^{13}C$-methamphetamine. See FIG. 11(*b*). Prepare as described above for a-19 but start with a-15.

Example 29

($^{15}N$-methamphetamine) a-21

This example describes the synthesis of $^{15}N$-methamphetamine. See FIG. 11(*c*). Prepare as described above for a-19 but start with a-17.

Examples 30-31

Synthesis of Labeled Methadone

Intermediate m-2: $^{13}C$-ethylmagnesium bromide

To 180 mmol magnesium in 30 mL dry diethyl ether is added dropwise 30 mL of a 6 M solution of $^{13}C$-ethylbromide m-1 (180 mmol). The ethylbromide is added at a rate that maintains moderate boiling of the solvent. After 1-1.5 hr refluxing the resulting 3 M solution of ethylmagnesiumbromide m-2 is used directly. See Novakov and co-workers *Chem. Res. Toxicol.* (2001), 14, 1239-1246.

Intermediate m-4: $D_3$-ethylmagnesium bromide m-4

To 180 mmol magnesium in 30 mL dry diethyl ether is added dropwise 30 mL of a 6 M solution of $D_3$-ethylbromide m-3 (180 mmol). The ethylbromide is added at a rate that maintains moderate boiling of the solvent. After 1-1.5 hr refluxing the resulting 3 M solution of ethylmagnesiumbromide m-4 is used directly. See Novakov and co-workers *Chem. Res. Toxicol.* (2001), 14, 1239-1246.

Example 30

$^{13}$C—R-(−)-methadone (m-6)

Figure 12:
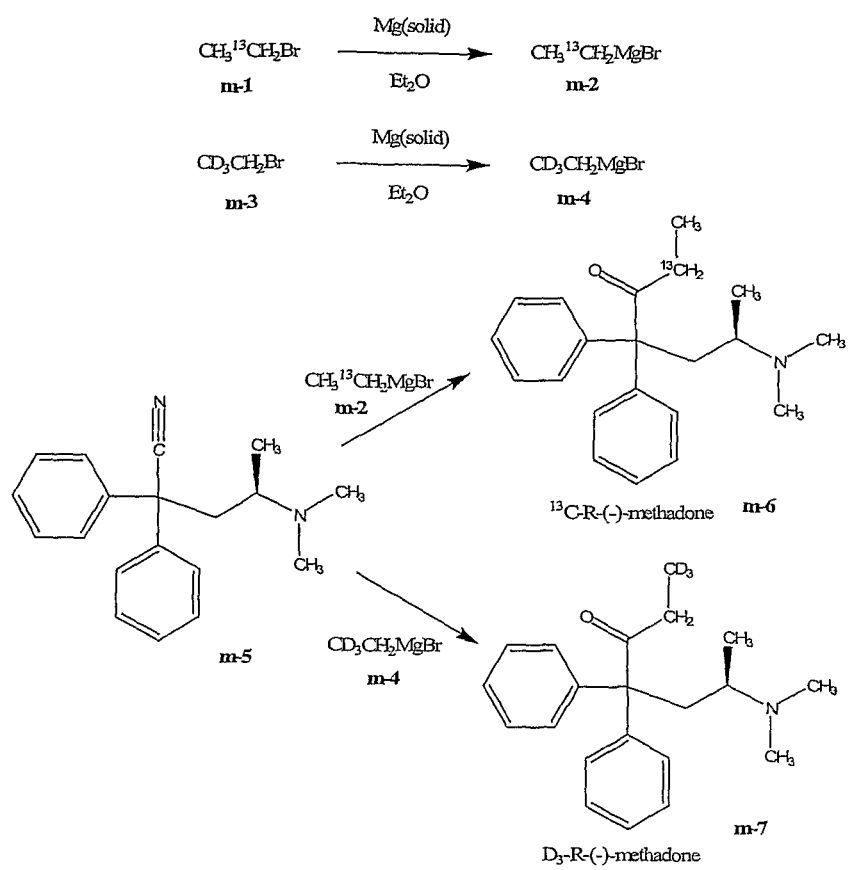
FIG. 12 shows the synthetic pathway for single labeled methadone.

This example describes the synthesis of labeled methadone. See FIG. 12.

All apparatus are dried and the reaction is carried out under an inert atmosphere of argon. A solution of (R)-(−)-2,2-diphenyl-4-dimethylaminopentanenitrile m-5 (5.0 g, 0.018 mol) in toluene (15 mL) is added to a stirred solution of 3 M $^{13}$C-ethylmagnesium bromide m-2 in ether (10.7 mL, 0.03 mol). The ether is removed under reduced pressure and the remaining solution is heated at reflux (135-140° C.) for 3 h. The solution will go slightly cloudy. After cooling to room temperature 2N HCl (30 mL) is added with care and then stirring is continued at 135-140° C.) for a further 30 min. The two phases are allowed to separate and cool to room temperature. After scratching the sides of the flask, a solid will start to crystallize from the aqueous phase. The flask should be cooled to complete crystallization and the white solid collected by filtration. This solid is then recrystallized from water to yield 2.7 g (43%) of (R)-(−)-methadone hydrochloride m-6. See Hull and co-workers, *Tetrahedron: Asymmetry* (2003), 14, 567-576 for a description of the synthesis of m-5.

Example 31

D$_3$-R-(−)-methadone (m-7)

As described above for $^{13}$C—R-(−)-methadone m-6 but substitute D3-ethylmagnesium bromide m-4 in place of $^{13}$C-ethylmagnesium bromide m-2. See Hull and co-workers, *Tetrahedron. Asymmetry* (2003), 14, 567-576]

Examples 32-33

Synthesis of Deuterated Morphine

Figure 13:
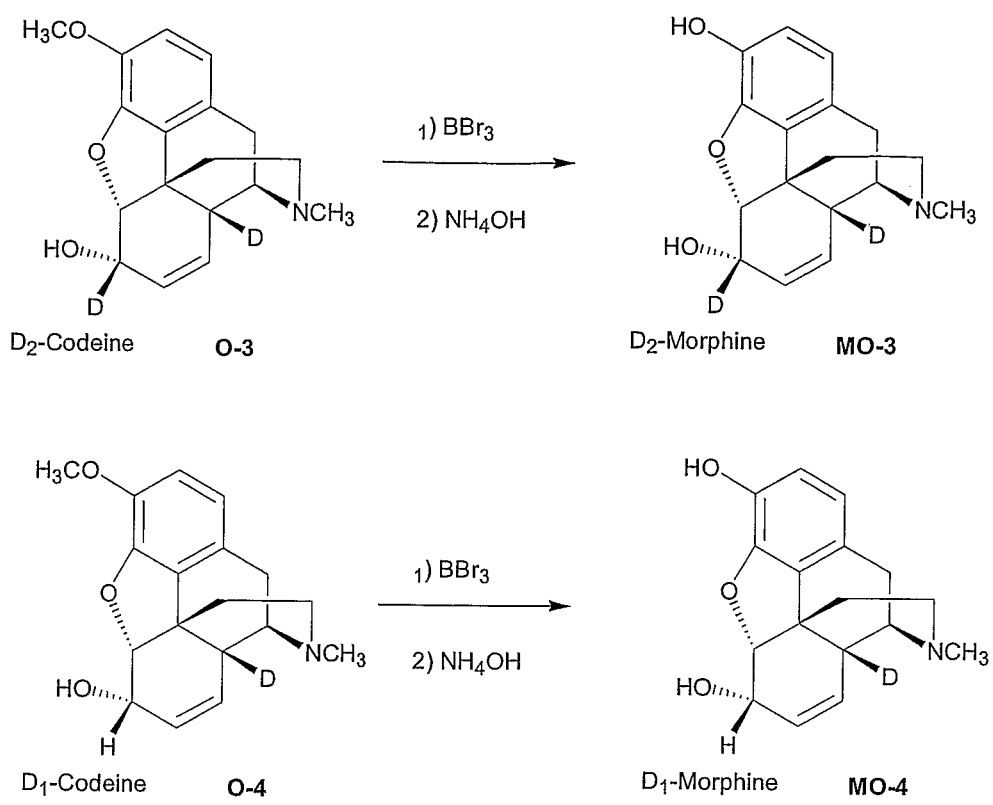
FIG. 13 shows the synthetic pathway for single and double $^2$H labeled morphine.

These examples describe the synthesis of deuterated morphine. See FIG. 13.

Example 32

D2-Morphine (MO-3)

Double $^2$H labeled morphine can be prepared using a modification of the procedure described in Journal of Medicinal Chemistry, 1977, vol 20, 164-165. A solution of 2.99 g (10 mmol) of anhydrous D2-Codiene O-3 in 25 ml of CHCl$_3$ is to be added during 2 min to a well-stirred solution of 15 g (59.9 mmol) of BBr$_3$ in 175 ml of CHCl$_3$ maintained in the range 23-26 degrees C. A 10 ml portion of CHCl$_3$, which is added to rinse the addition funnel, is added to the reaction mixture and stirring is continued for 15 min at 23-26 degrees C. The reaction mixture which will consist of a suspension of white solid (in CHCl$_3$) is then poured into a well-stirred mixture of 80 g of ice and 20 ml of concentrated (28-30% NH$_3$) NH$_4$OH. The two-phase system is kept at −5 to 0 degrees C. for 0.5 h (continuous stirring) and filtered. The resulting crystalline material is washed thoroughly with small portions of cold CHCl$_3$ and H$_2$O and dried to give 2.67 g (88.1%) of slightly off-white MO-3 monohydrate.

Example 33

D1-Morphine (MO-4)

Single $^2$H labeled morphine can be prepared using a modification of the procedure described in Journal of Medicinal Chemistry, 1977, vol 20, 164-165. A solution of 2.99 g (10 mmol) of anhydrous D2-Codiene O-3 in 25 ml of CHCl$_3$ is to be added during 2 min to a well-stirred solution of 15 g (59.9 mmol) of BBr$_3$ in 175 ml of CHCl3 maintained in the range 23-26 degrees C. A 10 ml portion of CHCl$_3$, which is added to rinse the addition funnel, is added to the reaction mixture and stirring is continued for 15 min at 23-26 degrees C. The reaction mixture which will consist of a suspension of white solid (in CHCl$_3$) is then poured into a well-stirred mixture of 80 g of ice and 20 ml of concentrated (28-30% NH$_3$) NH$_4$OH. The two-phase system is kept at −5 to 0 degrees C. for 0.5 h (continuous stirring) and filtered. The resulting crystalline material is washed thoroughly with small portions of cold CHCl$_3$ and H$_2$O and dried to give 2.67 g (88.1%) of slightly off-white MO-3 monohydrate.

Examples 34-36

Synthesis of Deuterated Hydromorphone

Figure 14:
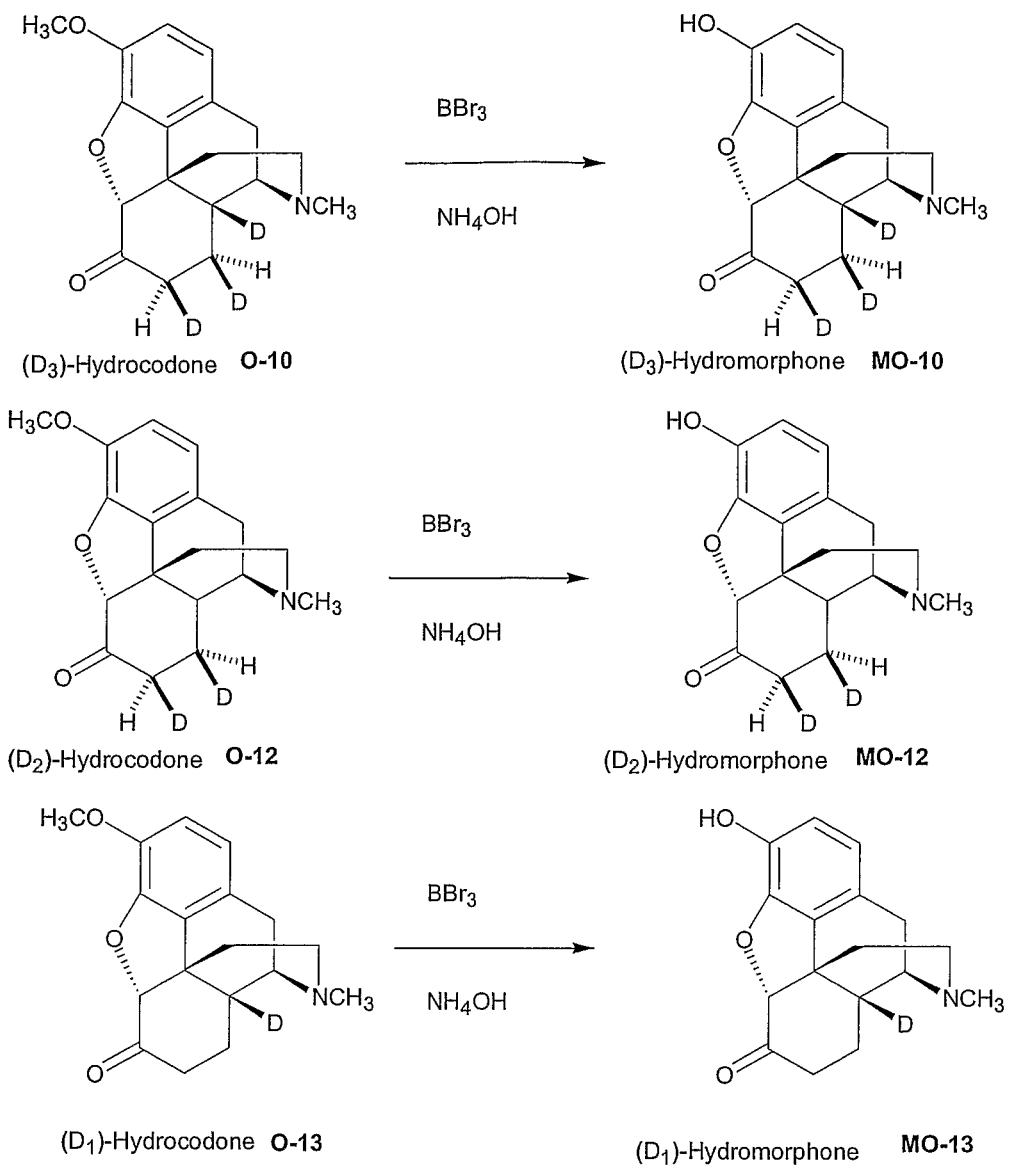
FIG. 14 shows the synthetic pathway for single, double, and triple $^2$H labeled hydromorphone.

These examples describe the synthesis of deuterated hydromorphone. See FIG. 14.

Example 34

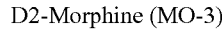
D3-Hydromorphone (MO-10)

Triple $^2$H labeled hydromorphone can be prepared using a modification of the procedure described in Journal of Medicinal Chemistry, 1977, vol 20, 164-165 and Tetrahedron Letters Vol. 25, 3335-3338, 1984. A solution of 2.99 g (10 mmol) of anhydrous D2-Hydrocodone O-10 in 25 ml of CHCl$_3$ is to be added during 2 min to a well-stirred solution of 15 g (59.9 mmol) of BBr$_3$ in 175 ml of CHCl$_3$ maintained in the range 23-26 degrees C. A 10 ml portion of CHCl$_3$, which is added to rinse the addition funnel, is added to the reaction mixture and stirring is continued for 15 min at 23-26 degrees C. The reaction mixture which will consist of a suspension of white solid (in CHCl$_3$) is then poured into a well-stirred mixture of 80 g of ice and 20 ml of concentrated (28-30% NH$_3$) NH$_4$OH. The two-phase system is kept at −5 to 0 degrees C. for 0.5 h (continuous stirring) and filtered. The resulting crystalline material is washed thoroughly with small portions of cold CHCl$_3$ and H$_2$O and dried to give 2.67 g (88.1%) of slightly off-white MO-10 monohydrate.

Example 35

D2-Hydromorphone (MO-12)

Double $^2$H labeled hydromorphone can be prepared using a modification of the procedure described in Journal of Medicinal Chemistry, 1977, vol 20, 164-165 and Tetrahedron Letters Vol. 25, 3335-3338, 1984. A solution of 2.99 g (10 mmol) of anhydrous D2-Hydrocodone O-12 in 25 ml of CHCl$_3$ is to be added during 2 min to a well-stirred solution of 15 g (59.9 mmol) of BBr$_3$ in 175 ml of CHCl$_3$ maintained in the range 23-26 degrees C. A 10 ml portion of CHCl$_3$, which is added to rinse the addition funnel, is added to the reaction mixture and stirring is continued for 15 min at 23-26 degrees C. The reaction mixture which will consist of a suspension of white solid (in CHCl$_3$) is then poured into a well-stirred mixture of 80 g of ice and 20 ml of concentrated (28-30% NH$_3$) NH$_4$OH. The two-phase system is kept at −5 to 0 degrees C. for 0.5 h (continuous stirring) and filtered. The resulting crystalline material is washed thoroughly with small portions of cold CHCl$_3$ and H$_2$O and dried to give 2.67 g (88.1%) of slightly off-white MO-12 monohydrate.

Example 36

D1-Hydromorphone (MO-13)

Double $^2$H labeled hydromorphone can be prepared using a modification of the procedure described in Journal of Medicinal Chemistry, 1977, vol 20, 164-165 and Tetrahedron Letters Vol. 25, 3335-3338, 1984. A solution of 2.99 g (10 mmol) of anyhydrous D2-Hydrocodone O-13 in 25 ml of CHCl$_3$ is to be added during 2 min to a well-stirred solution of 15 g (59.9 mmol) of BBr$_3$ in 175 ml of CHCl$_3$ maintained in the range 23-26 degrees C. A 10 ml portion of CHCl$_3$, which is added to rinse the addition funnel, is added to the reaction mixture and stirring is continued for 15 min at 23-26 degrees C. The reaction mixture which will consist of a suspension of white solid (in CHCl$_3$) is then poured into a well-stirred mixture of 80 g of ice and 20 ml of concentrated (28-30% NH$_3$) NH$_4$OH. The two-phase system is kept at −5 to 0 degrees C. for 0.5 h (continuous stirring) and filtered. The resulting crystalline material is washed thoroughly with small portions of cold CHCl$_3$ and H$_2$O and dried to give 2.67 g (88.1%) of slightly off-white MO-13 monohydrate.

Examples 37-40

Synthesis of Labeled Zolpidem and Zolpidem Hemitartrate

Figure 15:
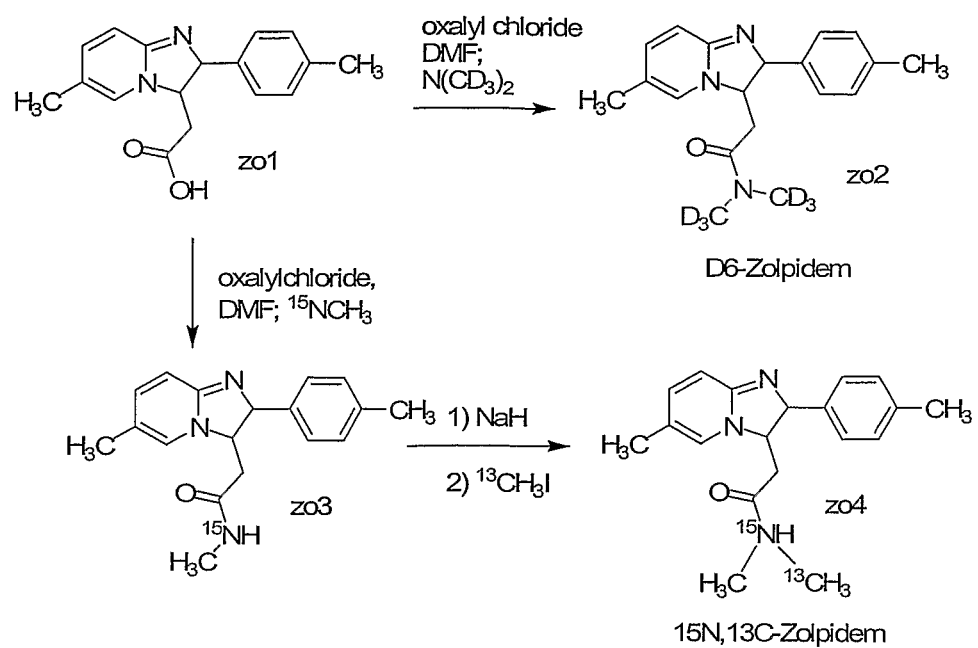
FIG. 15 shows the synthetic pathway for $^2$H labeled and $^{13}$C, $^{15}$N labeled zolpidem.

These examples describe the synthesis of labeled zolpidem and zolpidem hemitartrate. See FIG. 15.

Example 37

Synthesis of D6-Zolpidem, (zo2)

D6-Zolpidem can be prepared using a modification of the procedure described in U.S. Pat. No. 6,281,360. Suspend 5 g of 2-(p-tolyl)-6-methylimidazo[1,2a]pyridine-3-acetic acid zo1 in 50 ml of dry dichloromethane and add 2.5 g of oxalylchloride. Then, add slowly under stirring 5 drops of dimethylformamide (gas formation occurs) and, after 3 hours, add 1.1 g of oxalylchloride. Stir the reaction mixture for 1 hour then bubble slowly gaseous NH(CD$_3$)$_2$ through the reaction mixture for 1.5 hours. After termination, wash the reaction mixture with 2×10 ml of water, dry the organic phase with sodium sulfate and evaporate the solvent under reduced pressure. After adding 25 ml of ethyl acetate to the rest, a solid precipitates. Filter off the precipitate, wash with 2×5 ml of ethyl acetate and dry in a vacuum oven at 40 degrees C. The yield should be 4.3 g of zo2.

Example 38

Synthesis of 15N,13C-Zolpidem, (z04)

15N,13C-Zolpidem can be prepared using a modification of the procedure described in U.S. Pat. No. 6,281,360 and Tetrahedron 58 (2002) 8779-8791. Suspend 5 g of 2-(p-tolyl)-6-methylimidazo[1,2a]pyridine-3-acetic acid zo1 in 50 ml of dry dichloromethane and add 2.5 g of oxalylchloride. Then, add slowly under stirring 5 drops of dimethylformamide (gas formation occurs) and, after 3 hours, add 1.1 g of oxalylchloride. Stir the reaction mixture for 1 hour then bubble slowly gaseous $^{15}$NH$_2$CH$_3$ through the reaction mixture for 1.5 hours. After termination, wash the reaction mixture with 2×10 ml of water, dry the organic phase with sodium sulfate and evaporate the solvent under reduced pressure. After adding 25 ml of ethyl acetate to the rest, a solid precipitates. Filter off the precipitate, wash with 2×5 mil of ethyl acetate and dry in a vacuum oven at 40 degrees C. The yield should be 4.3 g of zo3.

To a solution of zo3 (1.63 mmol) in DMF will be added $^{13}$CH$_{3}$I (2.4 mmol) and 55 wt % of NaH (2.0 mmol) at 0 degrees C. After stirring for 3 h, the reaction mixture is quenched with sat. NH$_4$Cl (2 ml). The resulting mixture will be diluted with ether and washed with water and brine, dried over MgSO$_4$ and filtered. The filtrate will be evaporated in vacuo to give 508 mg of a crude product, which will be purified by silica gel column chromatography.

Examples 39-40

Synthesis of D6-Zolpidem Hemitartrate and 15N,13C-Zolpidem Hemitartrate

D6-Zolpidem hemitartrate and 15N, 13C-zolpidem hemitartrate can be prepared using a modification of the procedure described in U.S. Pat. No. 6,281,360. Dissolve 1 g of labeled zolpidem in 10 ml of methanol and add a solution of 0.244 g of L-tartaric acid in 5 ml of methanol. After cooling, white crystals are formed. Collect the solid by filtration, wash with cold methanol and dry.

Example 41

Synthesis of Deuterated Buprenorphine

Figure 16:
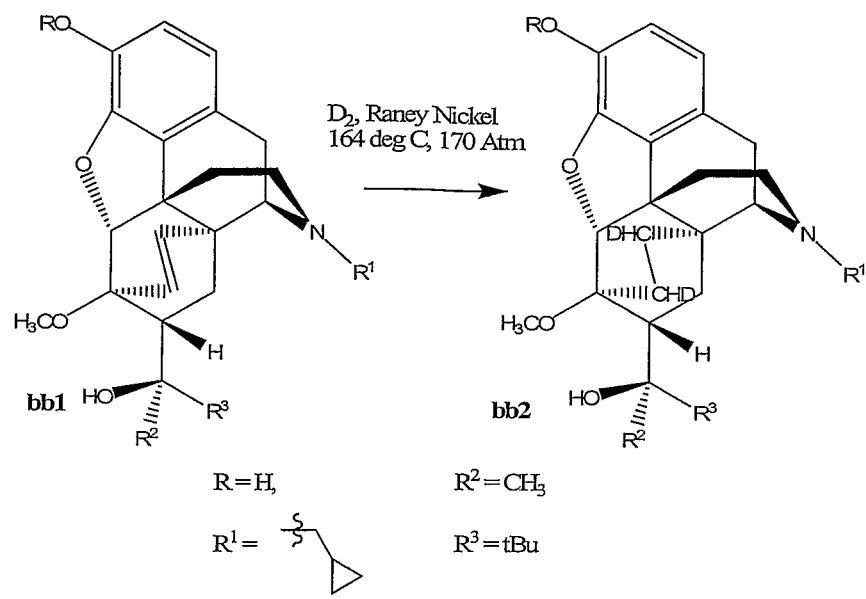
FIG. 16 shows the synthetic pathway for double $^2$H labeled buprenorphine.

This example describes the synthesis of deuterated buprenorphine. See FIG. 16. Deuterated buprenorphine can be prepared using a modification of the procedure described in GB1136214 and U.S. Pat. No. 3,433,791. Dissolve 40 g of bbl in ethanol (300 ml) and deuterate it with D$_2$ gas in the presence of Raney nickel catalyst (10 g) at 161-164 celsius and 164-182 atmosphere for four hours. Concentrate the solution after removing the catalyst by filtration will afford a white crystalline solid (26 g). This material is recrystallized from ethanol.

Example 42-46

Synthesis of Labeled Tramadol

Figure 17:
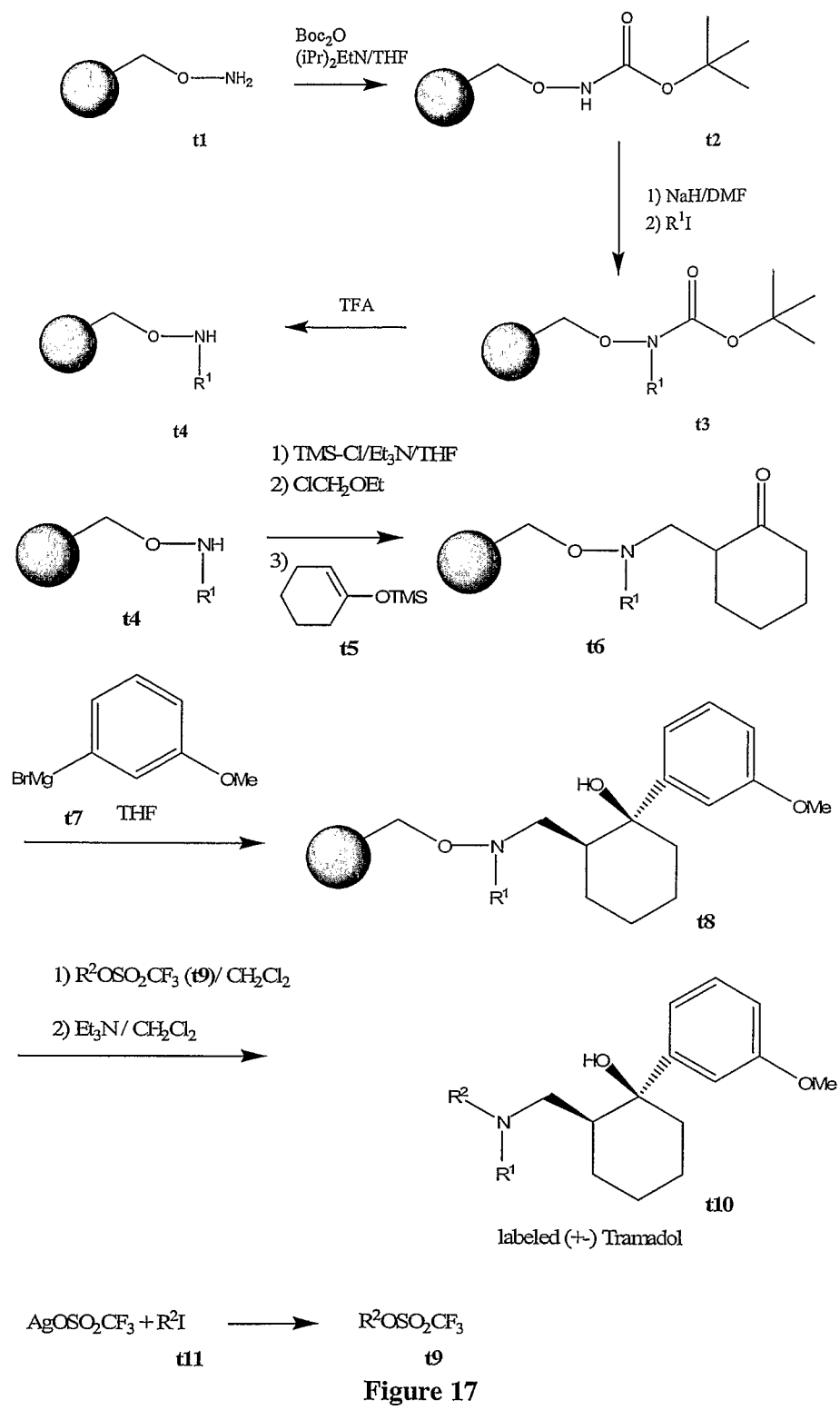
FIG. 17 shows the synthetic pathway for various $^{13}$C labeled tramadol.

These examples describe the synthesis of labeled tramadol. See FIG. 17.
General Procedure:
Various labeled tramadols can be prepared using a modification of the procedure described in Tetrahedron Letters 41 (2000) 6635-6638 and J. Org. Chem. 39, (1974) 3875-3877.
Methylated Hydroxylamine Resin t4:
To 2 g hydroxylamine resin t1 (0.5 mmol/gram loading) is added 2 mmol Boc anhydride and 2 mmol diisopropylethylamine in 10 ml THF and stirred for one hour. The resin is filtered and washed with dimethylformamide three times. To the resin is added 20 mmol NaH in dimethylformamide and the suspension is stirred for 16 h at room temperature. A quantity of 40 mmol of the labeled alkyl iodide R$^1$I is then added and stirred for another 16 h. The solution is filtered from the resin and the resin is washed with dimethylformamide several times. The resin is then treated with 20% trifluoroacetic acid in dichloromethane for 30 min after which it is filtered and washed three times with dimethylformamide. This will yield 1 mmol t4 on resin.

Labeled Tramadol t10:

To 2 g of methylated hydroxylamine resin t4 (1 mmol) is added 2 mmol trimethylsilyl chloride and 2 mmol triethylamine in 10 ml tetrahydrofuran. This suspension is stirred for one hour at room temperature. A quantity of 2 mmol chloromethylethyl ether is added to the suspension and stirred for 30 min at room temperature. Finally 2 mmol of cyclohexanone trimethylsilyl enol ether is added to the suspension and stirred for another hour at room temperature. The resin is then filtered and washed three times with tetrahydrofuran. The resin bound ketone t6 is then reacted with 3-methoxyphenyl magnesium bromide (10 mmol in 50 ml tetrahydrofuran) at room temperature for 16 h to give tertiary alcohol t8. The resin is then filtered and washed three tines with THF and three times with dichloromethane. The resin is then treated with labeled $R^{20}SO_2CF_3$ in dichloromethane (5 mmol $R^2OSO_2CF_3$ in 20 ml dichloromethane) for 16 h at room temperature. Finally the resin is treated with 5 mmol triethylamine in 20 ml dichloromethane at room temperature for 16 h to cleave the labeled tramadol t10 from the resin. The resin is filtered and the filtrate is dried under vacuum and purified by chromatography.

Labeled Methyl-Trifluorosulfonate:

Labeled methyl iodide (1 mmol) is added with stirring to 0.259 g (1 mmol) of silver triflate in 3 ml of carbon tetrachloride at ambient temperature. The solid silver iodide is filtered off and the labeled methyl triflate is isolated by removing the carbon tetrachloride in vacuo.

Example 42

Synthesis of 13C-Tramadol

Follow the above procedures, use $CH_3I$ for $R^1I$ and $^{13}CH_3I$ for $R^2I$.

Example 43

Synthesis of 13C2-Tramadol

Follow the above procedures, use $^{13}CH_3I$ for $R^1I$ and $^{13}CH_3I$ for $R^2I$.

Example 44

Synthesis of D3-Tramadol

Follow the above procedures, use $CH_3I$ for $R^1I$ and $CD_3I$ for $R^2I$.

Example 45

Synthesis of 13C,D3-Tramadol

Follow the above procedures, use $CH_3I$ for $R^1I$ and $^{13}CD_3I$ for $R^2I$.

Example 46

Synthesis of 13C2,D3-Tramadol

Follow the above procedures, use $^{13}CH_3I$ for $R^1I$ and $^{13}CD_3I$ for $R^2I$.

REFERENCES CITED

Numerous references, including patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entirety and to the same extent as if each reference was individually incorporated by reference.

The invention claimed is:

1. A method for monitoring use by a patient of a prescribed controlled drug to identify when a patient is using the controlled drug from sources other than as prescribed, the method comprising:
   (a) identifying a stable isotope that can be made part of the molecular structure of the controlled drug at a metabolically stable site thereof without affecting the pharmacologic activity of the controlled drug and wherein the stable isotope is retained on the molecular structure while it is in tissues or body fluid of a patient;
   (b) synthesizing an isotopically labeled version of the controlled drug by adding the stable isotope onto the molecular structure of the controlled drug;
   (c) prescribing the isotopically labeled version of the controlled drug to the patient;
   (d) recording the patient's prescription for the isotopically labeled version of the controlled drug in a registry;
   (e) testing a fluid or tissue sample from the patient for the presence of the controlled drug and, when detecting presence of the controlled drug, determining whether the detected controlled drug is the isotopically labeled version of the controlled drug found in the registry.

2. A method for monitoring use by a patient of a prescribed controlled drug to identify when a patient is using the controlled drug from sources other than as prescribed, the method comprising:
   (a) identifying a stable isotope that can be made part of the molecular structure of the controlled drug at a metabolically stable site thereof without affecting the pharmacologic activity of the controlled drug and wherein the stable isotope is retained on the molecular structure while it is in tissues or body fluid of a patient;
   (b) synthesizing an isotopically labeled version of the controlled drug by adding the stable isotope onto the molecular structure of the controlled drug;
   (c) prescribing the isotopically labeled version of the controlled drug to the patient;
   (d) recording the patient's prescription for the isotopically labeled version of the controlled drug in a registry;
   (e) accessing a patient's prescription in the registry;
   (f) periodically testing a fluid or tissue sample from the patient for the presence of the controlled drug and, when detecting presence of the controlled drug, determining whether the detected controlled drug is the isotopically labeled version of the controlled drug found in the registry.

3. A method for prescribing a controlled drug to a patient, which comprises
  (a) creating a drug registry containing information on prescriptions written for controlled drugs and the identity of the patient receiving such prescriptions,
  (b) recording all controlled drug prescriptions in the registry,
  (c) interrogating the drug registry for information on the patient, and
  (d) identifying a stable isotope that can be made part of the molecular structure of the controlled drug at a metabolically stable site thereof without affecting the pharmacologic activity of the controlled drug and wherein the stable isotope is retained on the molecular structure while it is in tissues or body fluid of a patient;
  (e) synthesizing an isotopically labeled version of the controlled drug by adding the stable isotope onto the molecular structure of the controlled drug;
  (f) prescribing the isotopically labeled version of the controlled drug to the patient only if the patient does not have an unexpired prescription for the same controlled drug recorded in the registry.

4. The method of claim 3, further comprising testing tissue or body fluid of the patient for the presence of the controlled drug before the prescribing step.

5. The method of claim 4, further comprising recording the test results in the registry.

6. The method of any one of claim 1, 2, or 3, wherein the controlled drug is selected from the group consisting of buprenorphine, zolpidein, and tramadol.

7. The method of any one of claim 1, 2 or 4, wherein the testing step comprises testing the fluid or tissue sample for the presence of the isotopically labeled version of the controlled drug using gas or liquid chromatography and mass spectrometry.

8. The method of any one of claim 1, 2, or 3, wherein the controlled drug is a benzodiazepine.

9. The method of any one of claim 1, 2, or 3, wherein the controlled drug is an amphetamine.

10. The method of any one of claim 1, 2, or 3, wherein the controlled drug is methylphenidate.

11. The method of any one of claim 1, 2, or 3, wherein the controlled drug is an opioid.

12. The method according to any one of claim 1, 2, or 3, wherein the istopically labeled version of the controlled drug comprises a mixture of isotopically labeled versions of the controlled drug having different labels in a specified ratio.

13. The method of claim 11, wherein the opioid is morphine or hydromorphone.

* * * * *